(12) United States Patent
Polefko et al.

(10) Patent No.: US 9,358,390 B2
(45) Date of Patent: Jun. 7, 2016

(54) CONFIGURING ELECTRICAL STIMULATION TO TREAT A PATIENT

(75) Inventors: Richard J. Polefko, Parma, OH (US);
Steven E. Wilder, Ashland, OH (US);
Scott G. Leyh, Cleveland Heights, OH (US)

(73) Assignee: NUVECTRA CORPORATION, Plano, TX (US)

( * ) Notice: Subject to any disclaimer, the term of this patent is extended or adjusted under 35 U.S.C. 154(b) by 0 days.

(21) Appl. No.: 13/226,956

(22) Filed: Sep. 7, 2011

(65) Prior Publication Data

US 2013/0060301 A1 Mar. 7, 2013

(51) Int. Cl.
*A61N 1/36* (2006.01)
*A61N 1/372* (2006.01)

(52) U.S. Cl.
CPC ........ *A61N 1/36071* (2013.01); *A61N 1/36017* (2013.01); *A61N 1/36021* (2013.01); *A61N 1/36132* (2013.01); *A61N 1/36185* (2013.01); *A61N 1/37247* (2013.01)

(58) Field of Classification Search
CPC ........... A61N 1/36071; A61N 1/36132; A61N 1/37247
USPC ...................................................... 607/46, 59
See application file for complete search history.

(56) References Cited

U.S. PATENT DOCUMENTS

| | | | |
|---|---|---|---|
| 5,938,690 A * | 8/1999 | Law et al. ........................ | 607/46 |
| 6,622,048 B1 | 9/2003 | Mann et al. | |
| 6,909,917 B2 | 6/2005 | Woods et al. | |
| 7,216,000 B2 | 5/2007 | Sieracki et al. | |
| 7,463,927 B1 * | 12/2008 | Chaouat .......................... | 607/46 |
| 7,617,002 B2 | 11/2009 | Goetz | |
| 7,623,918 B2 * | 11/2009 | Goetz .............................. | 607/27 |
| 7,822,483 B2 | 10/2010 | Stone et al. | |
| 7,881,805 B2 | 2/2011 | Bradley et al. | |
| 7,890,182 B2 | 2/2011 | Parramon et al. | |
| 7,933,655 B2 | 4/2011 | Sieracki et al. | |

(Continued)

FOREIGN PATENT DOCUMENTS

WO 2009/134480 11/2009

OTHER PUBLICATIONS

Extended European Search Report for Application No. 12182113.6 dated Oct. 4, 2012 (7 pages).

(Continued)

*Primary Examiner* — George Evanisko
(74) *Attorney, Agent, or Firm* — Haynes & Boone, LLP; Eric Li

(57) ABSTRACT

A stimulation system, such as a spinal cord stimulation (SCS) system, having a programmer with a user interface. The programmer determines a position of an implanted medical lead with respect to a patient's spinal column. The programmer overlays the medical lead, an initial stimulation field, and an initial target stimulation area within the initial stimulation field on an image of the spinal column. A user enters, via the user interface, graphical manipulations of displayed boundaries of the initial stimulation field and the initial target stimulation area. The graphical manipulations of the stimulation field and the target stimulation field are independent of each other and they may move and/or alter the shape of the boundaries. The programmer then determines stimulation parameters to drive the implanted medical lead to generate the displayed stimulation field and target stimulation field as manipulated by the user.

20 Claims, 20 Drawing Sheets

(56) References Cited

U.S. PATENT DOCUMENTS

| | | | |
|---|---|---|---|
| 2001/0007950 | A1 | 7/2001 | North et al. |
| 2001/0034542 | A1 | 10/2001 | Mann |
| 2005/0119714 | A1 | 6/2005 | Sieracki et al. |
| 2006/0241720 | A1 | 10/2006 | Woods et al. |
| 2006/0241721 | A1 | 10/2006 | Kothandaraman et al. |
| 2006/0293720 | A1 | 12/2006 | DiLorenzo |
| 2007/0032834 | A1 | 2/2007 | Gliner et al. |
| 2007/0167991 | A1 | 7/2007 | DiLorenzo et al. |
| 2007/0203538 | A1 | 8/2007 | Stone et al. |
| 2008/0004674 | A1 | 1/2008 | King et al. |
| 2008/0215118 | A1* | 9/2008 | Goetz et al. ............ 607/59 |
| 2008/0215119 | A1 | 9/2008 | Woods et al. |
| 2009/0018617 | A1 | 1/2009 | Skelton et al. |
| 2009/0281596 | A1 | 11/2009 | King et al. |
| 2009/0306746 | A1 | 12/2009 | Blishak |
| 2010/0135553 | A1 | 6/2010 | Joglekar |
| 2010/0274320 | A1 | 10/2010 | Torgerson |
| 2010/0292751 | A1 | 11/2010 | Choi et al. |
| 2011/0040351 | A1* | 2/2011 | Butson et al. ............ 607/59 |
| 2011/0040546 | A1 | 2/2011 | Gerber et al. |
| 2011/0093043 | A1* | 4/2011 | Torgerson et al. ....... 607/59 |
| 2011/0208012 | A1* | 8/2011 | Gerber et al. ............ 600/300 |
| 2011/0307032 | A1* | 12/2011 | Goetz et al. ............ 607/59 |
| 2012/0116476 | A1 | 5/2012 | Kothandaraman |
| 2012/0165898 | A1 | 6/2012 | Moffitt |
| 2012/0265271 | A1 | 10/2012 | Goetz |
| 2013/0296972 | A1 | 11/2013 | Polefko et al. |

OTHER PUBLICATIONS

Extended European Search Report for Application No. 12182115.1 dated Oct. 30, 2012 (7 pages).

Extended European Search Report for Application No. 12182119.3 dated Oct. 22, 2012 (8 pages).

Extended European Search Report for Application no. 12182121.9 dated Oct. 26, 2012 (8 pages).

United States Patent Office Action for U.S. Appl. No. 13/226,939 dated Nov. 9, 2012 (8 pages).

United States Patent Office Action for U.S. Appl. No. 13/226,897 dated Dec. 13, 2012 (7 pages).

Freescale Semiconductor, Inc., "i.MX51 Applications Processors for Consumer and Industrial Products," Data Sheet: Technical Data, Document No. IMX51CEC, Rev. 4 (Aug. 2010) 200 pages.

Holsheimer, J., "Computer modelling of spinal cord stimulation and its contribution to therapeutic efficacy," Spinal Cord (1998) 36:531-540.

North, R.B. et al., "Patient-interactive, computer-controlled neurological stimulation system: clinical efficacy in spinal cord stimulator adjustment," J. Neurosurg. (1992) 76(6):967-972, http://www.ncbi.nlm.nih.gov/pubmed/1588431.

Press Release, "New neurostimulation patient programming software enables more thorough and efficient . . . " from http://phx.corporate-ir.net/phoenix...6/3&highlight= (May 12, 2009) 2 pages.

Texas Instruments Inc., "Mixed Signal Microcontroller," brochure, MSP430G2x32, MSP430G2x02; SLAS723 (Dec. 2010) 53 pages.

Virtualmedicalcentre.com, "Spinal Cord Stimulation Devices," http://www.virtualmedicalcentre.com/devices.asp?sid=2 (Nov. 1, 2008) 7 pages.

United States Patent Office Action for U.S. Appl. No. 13/226,969 dated Dec. 20, 2012 (6 pages).

United States Patent Office Notice of Allowance for U.S. Appl. No. 13/226,969 dated Mar. 4, 2013 (5 pages).

United States Patent Office Action for U.S. Appl. No. 13/226,939 dated Feb. 25, 2013 (7 pages).

United States Patent Office Examiner's Interview Summary for U.S. Appl. No. 13/226,897 dated Jun. 13, 2013 (3 pages).

United States Patent Office Final Rejection for U.S. Appl. No. 13/226,897 dated Sep. 9, 2013 (8 pages).

United States Patent Office Final Rejection for U.S. Appl. No. 13/226,939 dated Nov. 15, 2013 (7 pages).

United States Patent Office Action for U.S. Appl. No. 13/937,463 dated Dec. 5, 2013 (9 pages).

United States Patent Notice of Allowance for U.S. Appl. No. 13/226,897 dated Mar. 6, 2014 (9 pages).

United States Patent Office Interview Summary for U.S. Appl. No. 13/226,897 dated Mar. 21, 2014 (3 pages).

United States Patent Office Action for U.S. Appl. No. 13/226,939 dated Apr. 4, 2014 (8 pages).

United States Patent Office Action for U.S. Appl. No. 13/937,463 dated Jun. 5, 2014 (10 pages).

United States Patent Office Final Rejection for U.S. Appl. No. 13/226,939 dated Aug. 11, 2014 (9 pages).

* cited by examiner

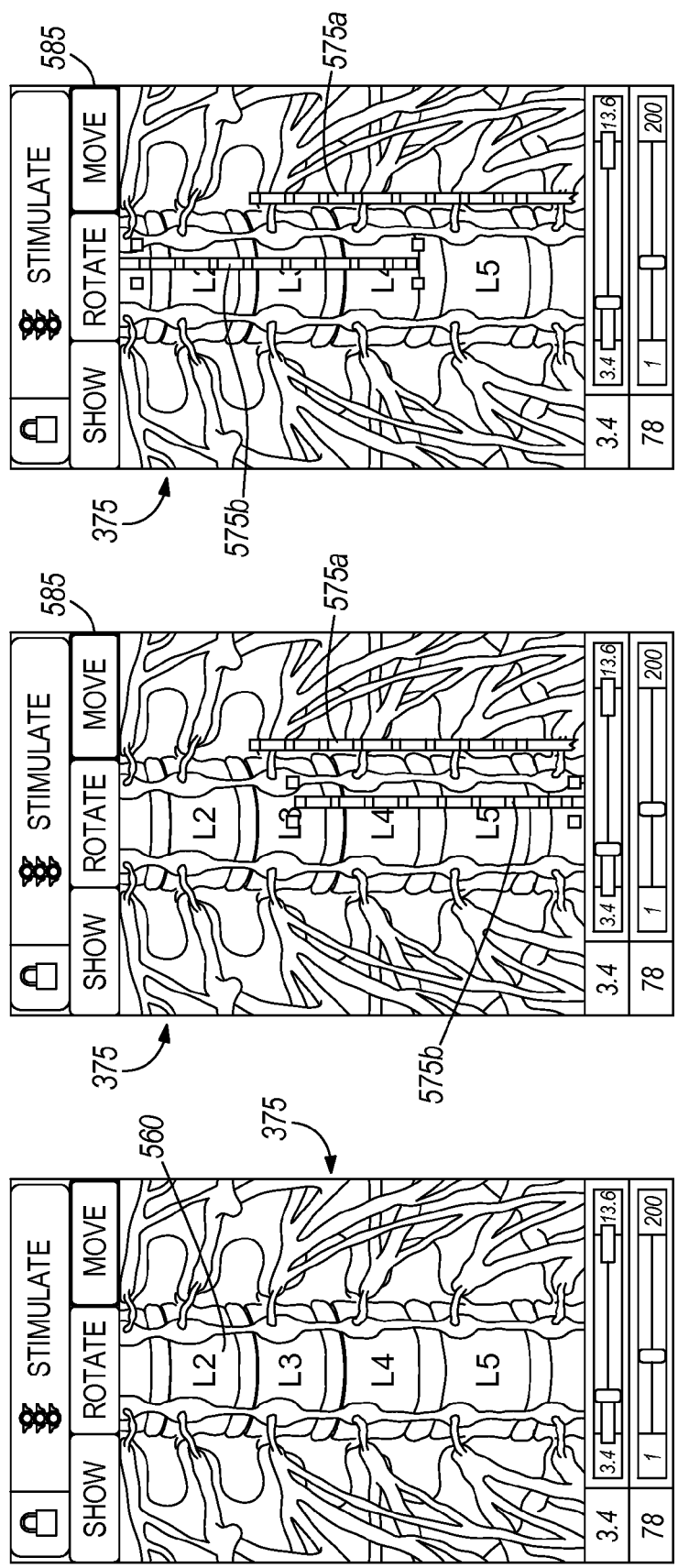

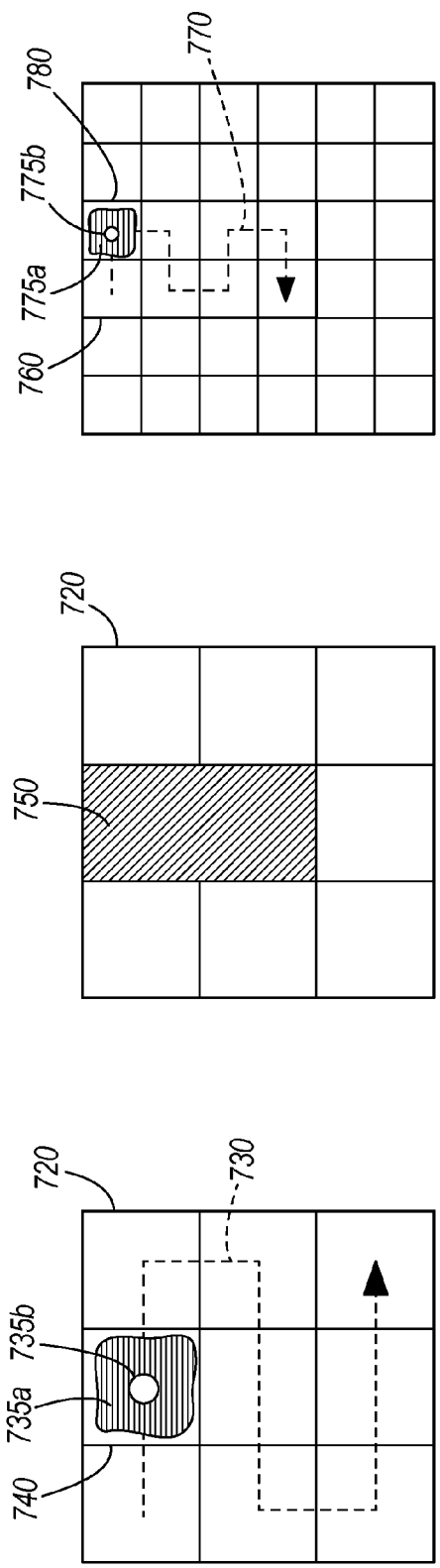
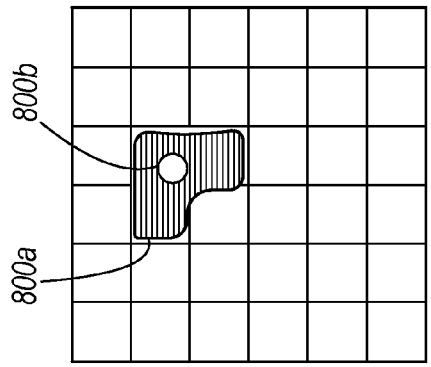
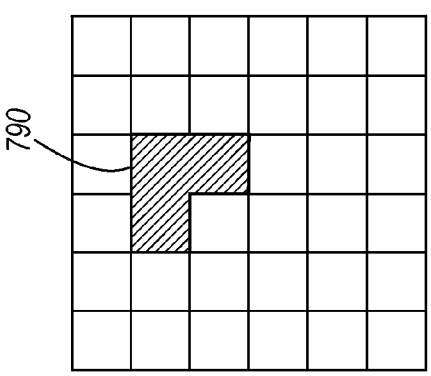
FIG. 19A
FIG. 19B
FIG. 19C
FIG. 19D
FIG. 19E

CONFIGURING ELECTRICAL STIMULATION TO TREAT A PATIENT

BACKGROUND

The invention relates to a stimulation system, such as a spinal cord stimulation (SCS) system, having a tool for programming an electrical stimulation generator, such as an implantable pulse generator (IPG), of the system. The invention also relates to a method for developing a program for the stimulation system.

A spinal cord stimulator is a device used to provide electrical stimulation to the spinal cord or spinal nerve neurons for managing pain. The stimulator includes an implanted or external pulse generator and an implanted medical electrical lead having one or more electrodes at a distal location thereof. The pulse generator provides the stimulation through the electrodes via a body portion and connector of the lead. Spinal cord stimulation programming is defined as the discovery of the stimulation electrodes and parameters that provide the best possible pain relief (or paresthesia) for the patient using one or more implanted leads and its attached pulse generator. The programming is typically achieved by selecting individual electrodes and adjusting the stimulation parameters, such as the shape of the stimulation waveform, amplitude of current in mA (or amplitude of voltage in V), pulse width in microseconds, frequency in Hz, and anodic or cathodic stimulation.

With newer medical electrical leads having an increased number of electrodes, the electrode and parameter combination increases exponentially. This results in a healthcare professional, such as a clinician, requiring a substantial amount of time for establishing a manually created program for providing therapeutic spinal cord stimulation. Therefore, a manual approach for creating a program is not an optimal solution for the SCS system.

SUMMARY

Numerous embodiments of the invention provide a method and system for programming an SCS system with a substantially reduced time requirement, increased accuracy, and reduced power requirements.

In some embodiments, the invention provides a method of configuring electrical stimulation to treat a patient with a stimulation system. The stimulation system includes an electrical stimulation generator, an implanted medical lead, implanted in the patient and coupled to the electrical stimulation generator, and a programmer with a display screen. The method includes displaying an image of a tissue (such as a spinal column) on the display screen of the programmer and determining a position of the implanted medical lead with respect to the tissue, an initial stimulation field, and an initial target stimulation area within the initial stimulation field. The programmer then displays the medical lead, the initial stimulation field, and the initial target stimulation area on the image of the tissue. The initial stimulation field has an initial boundary depicted on the display screen and the initial target stimulation area has an initial target boundary depicted on the display screen. The programmer receives graphical manipulations of the initial boundary and the initial target boundary to define an altered stimulation field and an altered target stimulation area. The graphical manipulations at least one of move and alter the shape of the initial boundary and the initial target boundary. The programmer then determines stimulation parameters to drive the implanted medical lead to generate the altered stimulation field and the altered target stimulation area. The method then includes driving, with the electrical stimulation generator, the implanted medical lead according to the determined stimulation parameters.

In other embodiments, the invention provides a stimulation system for providing electrical stimulation to treat a patient. The stimulation system includes an electrical stimulation generator, an implanted medical lead coupled to the electrical stimulation generator, and a programmer. The programmer includes a communication unit that communicates with the electrical stimulation generator to program electrical stimulation, a display screen that displays an image of a spinal column and a position of the at least one medical lead relative to the spinal column, and a user interface. The programmer is configured to determine a position of the implanted medical lead with respect to the spinal column, an initial stimulation field, and an initial target stimulation area within the initial stimulation field. The programmer is further configured to display the medical lead, the initial stimulation field, and the initial target stimulation area on the image of the spinal column. The initial stimulation field has an initial boundary depicted on the display screen and the initial target stimulation area has an initial target boundary depicted on the display screen. The programmer receives, via the user interface, graphical manipulations of the initial boundary and the initial target boundary to define an altered stimulation field and an altered target stimulation area. The graphical manipulations at least one of move and alter the shape of the initial boundary and the initial target boundary. The programmer then determines stimulation parameters to drive the implanted medical lead to generate the altered stimulation field and the altered target stimulation area. Furthermore, the programmer programs the electrical stimulation generator to generate electrical stimulation with the implanted medical lead according to the determined stimulation parameters.

In other embodiments, the invention provides a computer readable medium including a set of program instructions that are executed by a processor of a programmer. The execution of the instructions causes the programmer to display an image of a spinal column of a patient on a display screen of the programmer and to determine a position of an implanted medical lead with respect to the spinal column, an initial stimulation field, and an initial target stimulation area within the initial stimulation field. The programmer further displays, on the display screen, the medical lead, the initial stimulation field, and the initial target stimulation area on the image of the spinal column. The initial stimulation field has an initial boundary depicted on the display screen and the initial target stimulation area has an initial target boundary depicted on the display screen. The programmer further receives graphical manipulations of the initial boundary and the initial target boundary to define an altered stimulation field and an altered target stimulation area. The graphical manipulations at least one of move and alter the shape of the initial boundary and the initial target boundary. The programmer then determines stimulation parameters to drive the implanted medical lead to generate the altered stimulation field and the altered target stimulation area. The execution of the instructions then cause the programmer to program an electrical stimulation generator to generate electrical stimulation with the implanted medical lead according to the determined stimulation parameters.

Other aspects of the invention will become apparent by consideration of the detailed description and accompanying drawings.

BRIEF DESCRIPTION OF THE DRAWINGS

FIGS. 12A-I illustrate a graphical user interface for modeling the position of medical leads and electrical stimulation on a patient spinal column.

FIGS. 19A-E also illustrate a graphical user interface for automated programming.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

The invention herein relates to an electrical stimulation system for providing stimulation to target tissue of a patient. The system described in detail below is a spinal cord stimulation (SCS) system for providing electrical pulses to the neurons of the spinal cord of a patient. However, many aspects of the invention are not limited to spinal cord stimulation. The electrical stimulation system may provide stimulation to other body portions including a muscle or muscle group, nerves, the brain, etc.

Figure 1:
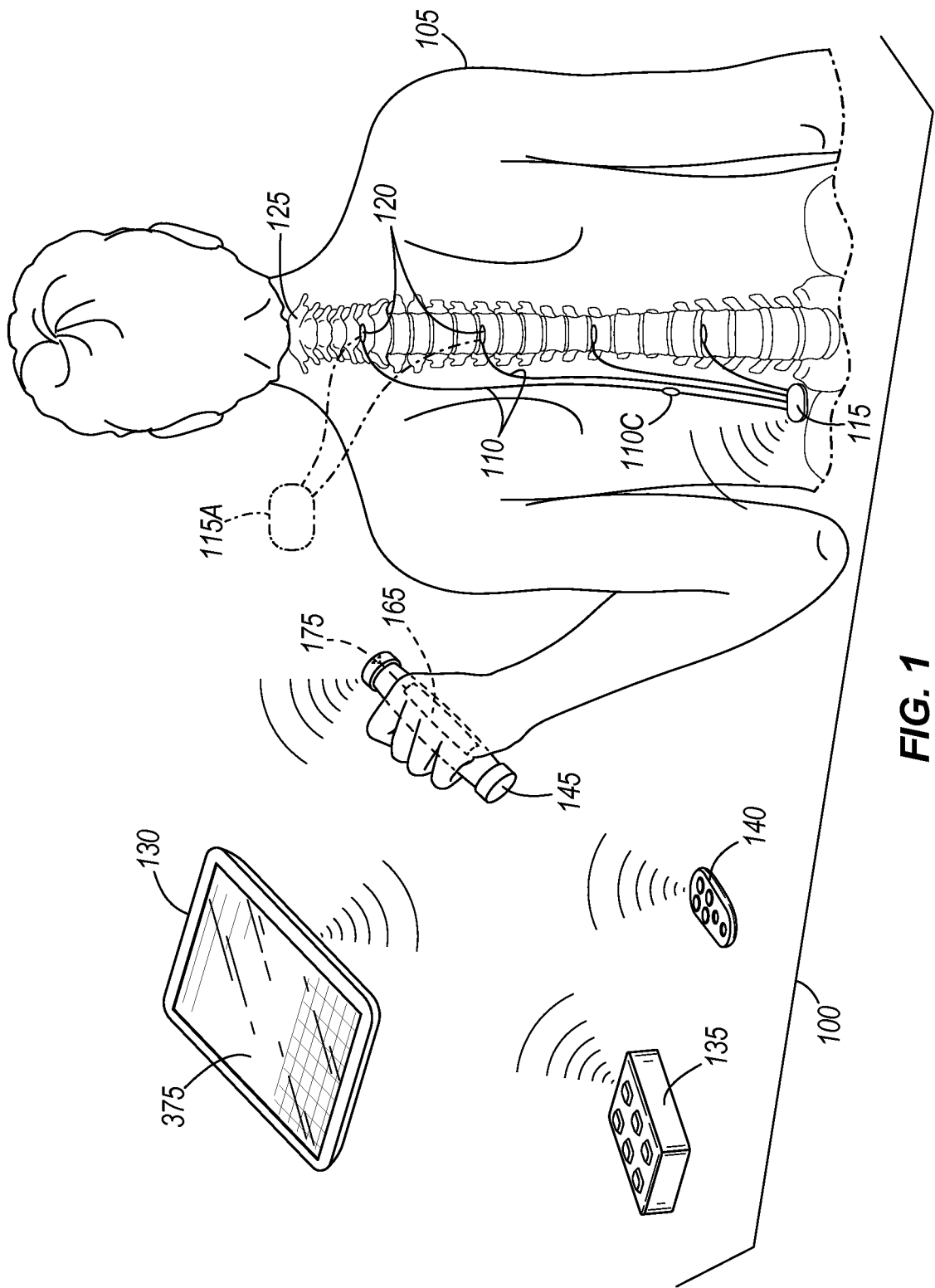
FIG. 1 is a partial perspective view of a patient using a spinal cord stimulation system.

FIG. 1 shows a spinal cord stimulation system 100 in use with a patient 105. The system 100 includes one or more implanted medical electrical leads 110 connected to an implantable pulse generator (IPG) 115 or external pulse generator (EPG) 115A. The leads 110 include an electrode array 120 at a distal end of the base lead cable. The electrode array 120 includes one or more electrical stimulation electrodes (may also be referred as electrode contacts or simply electrodes) and is placed adjacent to the dura of the spine 125 using an anchor. The spinal column includes the C1-C7 (cervical), T1-T12 (thoracic), L1-L5 (lumbar) and S1-S6 (sacral) vertebrae and the electrode array(s) 120 may be positioned anywhere along the spine 125 to deliver the intended therapeutic effects of spinal cord electrical stimulation in a desired region of the spine. The electrodes (discussed further in FIGS. 2 and 3) of the electrode arrays 120 promote electrical stimulation to the neurons of the spine based on electrical signals generated by the IPG 115. In one construction, the electrical signals are regulated current pulses that are rectangular in shape. However, the electrical signals can be other types of signals, including other types of pulses (e.g., regulated voltage pulses), and other shapes of pulses (e.g., trapezoidal, sinusoidal). The stimulation is provided from the IPG 115 to the electrodes via the base lead, which is connected to the IPG 115 with the proximal end of the base lead. The body of the lead can traverse through the body of the patient via the spinal column and from the spinal column through the body of the patient to the implant site of the IPG 115.

The IPG 115 generates the electrical signals through a multiplicity of electrodes (e.g., four, eight, sixteen, twenty-four electrodes). The IPG 115 can control, for example, six aspects of electrical stimulation based on a program (may also be referred to as a protocol): on/off, amplitude (e.g., current or voltage), frequency, pulse width, pulse shape, and polarity (anodic or cathodic stimulation). The stimulation most discussed herein is a regulated (or constant) current that provides a square wave, cathodic stimulation with a variable amplitude, frequency, and/or pulse width. Typically, the IPG 115 is implanted in a surgically made pocket (e.g., in the abdomen) of the patient. However, the pulse generator can also be the EPG 115A.

The IPG 115 communicates with any one of a clinician programmer (CP) 130, a patient programmer and charger (PPC) 135, and a pocket (or fob) programmer (PP) 140. As discussed in further detail below, the CP 130 interacts with the IPG 115 to develop a program for stimulating the patient. The developing of the program is assisted with the use of a patient-feedback device (PFD) 145. Once a program is developed, the program may be stored at the IPG 115. The PPC 135 or the PP 140 can activate, deactivate, or perform limited changes to the programming parameters of the program. The PPC 135 is also used for charging the IPG 115.

For the construction described herein, the IPG 115 includes a rechargeable, multichannel, radio-frequency (RF) programmable pulse generator housed in a metallic (e.g., titanium) case or housing. The metallic case is sometimes referred to as the "can" and may act either as a cathode or an anode or floating to the electrical contacts.

Figure 2:
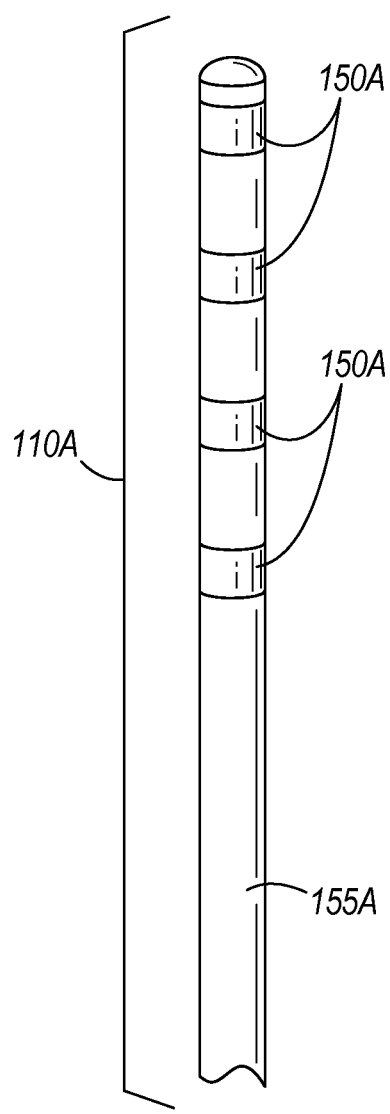
FIG. 2 is a perspective view of an in-line lead for use in the spinal cord stimulation system of FIG. 1.
Figure 3:
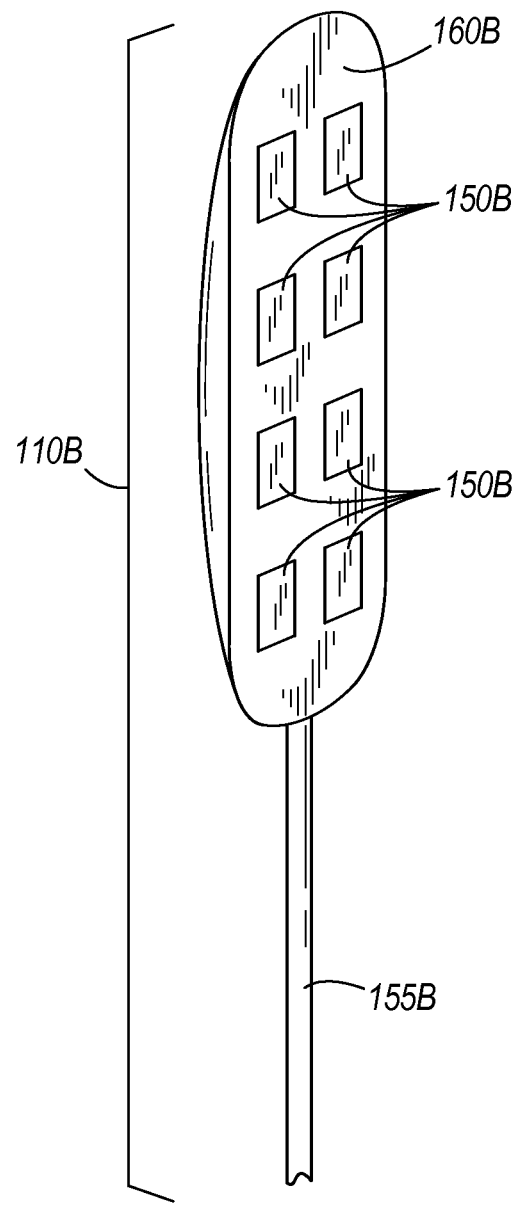
FIG. 3 is a perspective view of a paddle lead for use in the spinal cord stimulation system of FIG. 1.

Referring now to FIGS. 2 and 3, the figures show two exemplary leads 110A and 110B, respectively, that can be used in the SCS system. A first common type of lead 110 is the "in-line" lead shown in FIG. 2. An in-line lead 110A includes individual electrodes 150A along the length of a flexible cable 155A. A second common type of lead 110 is the "paddle" lead shown in FIG. 3. In general, the paddle lead 110B is shaped with a wide platform 160B on which a variety of electrode 150B configurations are situated. For example, the paddle lead 110B shown in FIG. 3 has two columns of four rectangular shaped electrodes 150B. A paddle lead typically contains contacts on one side only, but is not restricted to individual electrodes on either side, or electrodes perforating the carrier material.

For both leads shown in FIGS. 2 and 3, a flexible cable 155A or 155B has respective small wires for the electrodes 150A or 150B. The wires are embedded within the cable 155A or 155B and carry the electrical stimulation from the IPG 115 to the electrodes 150A or 150B.

It is envisioned that other types of leads 110 and electrode arrays 120 can be used with the invention. Also, the number of electrodes 150 and how the electrodes 150 are arranged in the electrode array 120 can vary from the examples discussed herein.

The leads shown in FIGS. 2 and 3 are multiple channel leads. Here, a "channel" is defined as a specified electrode 150, or group of electrodes 150, that receives a specified pattern or sequence of electrical stimuli. For simplicity, this description will focus on each electrode 150 and the IPG's 115 metallic housing providing a respective channel. When more than one channel is available, each channel may be programmed to provide its own stimulus to its defined electrode.

There are many instances when it is advantageous to have multiple channels for stimulation. For example, different pain locations (e.g., upper extremities, lower extremities) of the patient may require different stimuli. Further, some patients may exhibit conditions better suited to "horizontal" stimulation paths, while other patients may exhibit conditions better suited to "vertical" stimulation paths. Therefore, multiple electrodes positioned to provide multiple channels can cover more tissue/neuron area, and thereby provide better stimulation program flexibility to treat the patient.

It is also envisioned that the number of leads 110 can vary. For example, one, two, or more leads 110 can be connected to the IPG 115. The electrode arrays 120 of the leads 110, respectively, can be disposed in different vertical locations on the spine 125 with respect to a vertical patient 105, can be disposed horizontally (or "side-by-side") on the spine 125 with respect to a vertical patient 105, or some combination thereof.

In alternative to the IPG 115, the leads 110 can receive electrical stimuli from the EPG 115A (also referred to a trial stimulator) through one or more percutaneous lead extensions. The EPG 115A may be used during a trial period.

In one specific construction, a single lead 110B having a two-by-four electrode paddle (as shown in FIG. 3) is secured to the thoracic portion of the spine 125. An IPG 115 having a metallic housing is disposed within the patient 105. The housing acts as another electrode in this contemplated SCS system 100. Thus, this arrangement results in nine electrodes total. Also, the specifically-discussed system includes nine channels formed by the eight electrodes of the electrode array 120, respectively, and the metallic housing of the IPG 115. However, it contemplated that a different number of leads, electrodes, and channels fall within the scope of the invention.

Referring back to FIG. 1, a user provides feedback to the CP 130 with a PFD 145 while the CP 130 develops the program for the IPG 115. In FIG. 1, the PFD 145 is an ergonomic handheld device having a sensor (also referred to as input) 165, a controller, and a communications output 175. The sensor 165 can take the form of a discrete switch or can take the form of a continuously variable input, such as through the use of a strain gauge. It is envisioned that the use of a continuously variable input can provide magnitude information, thereby providing feedback information.

Figure 4:
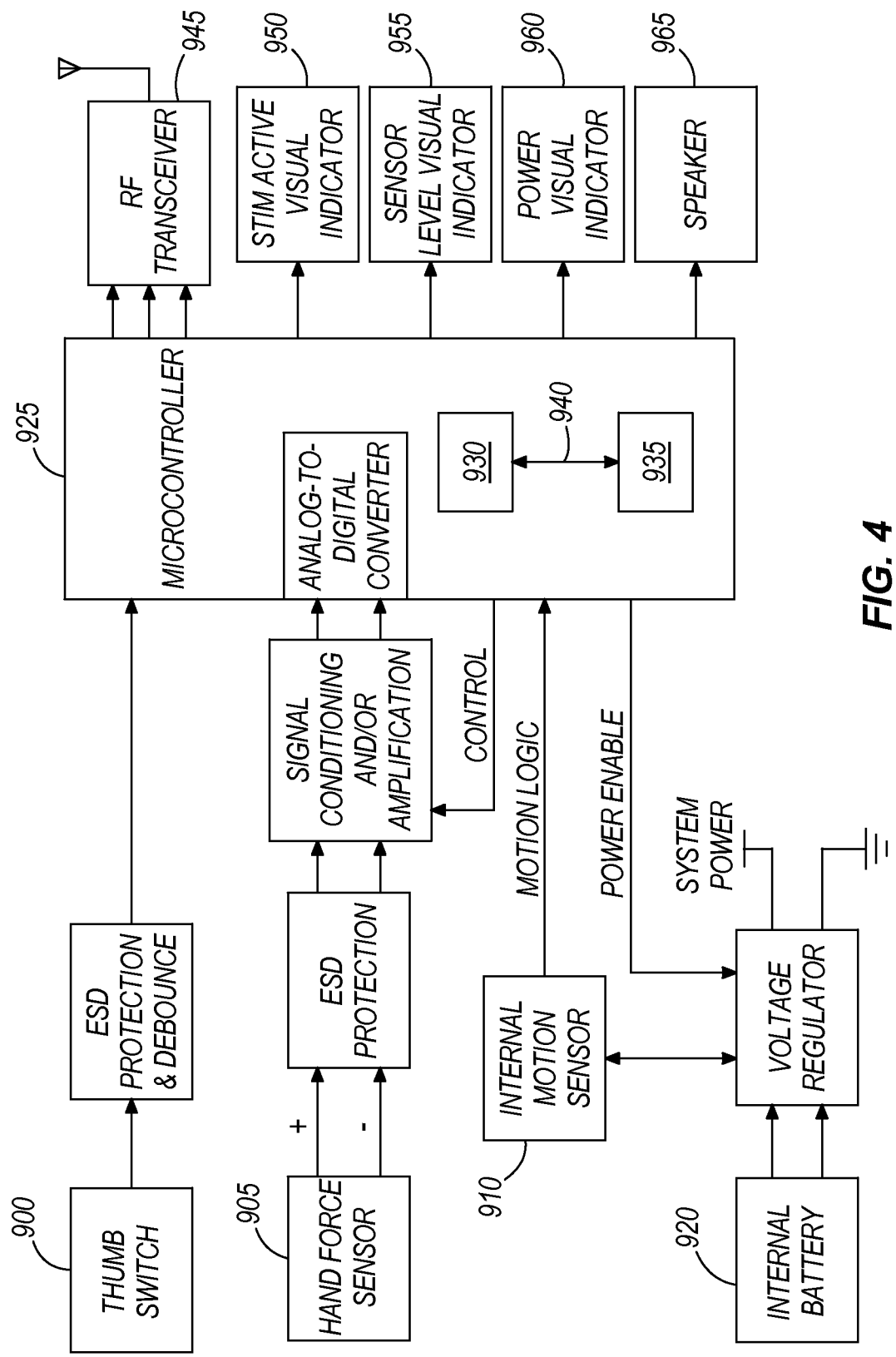
FIG. 4 is a block diagram of a patient-feedback device for use in the spinal cord stimulation system of FIG. 1.

FIG. 4 provides a block diagram of an exemplary handheld PFD 145 used in the SCS system 100. The PFD 145 includes two inputs 900 and 905 in communication with the housing of the device 145 and one input 910 internal to the housing. One of the external inputs 900 is a binary ON/OFF switch, preferably activated by the patient's thumb, to allow the patient 105 to immediately deactivate stimulation. The second input 905 includes a force or displacement sensor sensing the pressure or force exerted by the patient's hand. The sensed parameter can be either isotonic (constant force, measuring the distance traversed) or isometric (measuring the force, proportional to pressure applied by patient 105). The resulting signal from the sensor 905 is analog and, therefore, the signal is conditioned, amplified, and passed to a microcontroller via an analog-to-digital converter.

The internal input 910 for the PFD 145 of FIG. 4 is a motion sensor. The sensor 910, upon detecting motion, initiates activation of the PFD 145. The device 145 stays active until movement is not detected by the sensor 910 for a time period. Alternatively, the PFD can be activated/deactivate by an on-off button. Power is provided by an internal battery 920 that can be replaceable and/or rechargeable.

The processing of the inputs from the sensors 900 and 905 take place in a controller, such as a microcontroller 925. The microcontroller 925 includes a suitable programmable portion 930 (e.g., a microprocessor or a digital signal processor), a memory 935, and a bus 940 or other communication lines. Output data of the microcontroller 925 is sent via a Bluetooth bi-direction radio communication portion 945 to the CP 130. The Bluetooth portion 945 includes a Bluetooth communication interface, an antenna switch, and a related antenna, all of which allows wireless communication following the Bluetooth Special Interest Group standard. Other outputs may include indicators (such as light-emitting diodes) for communicating stimulation activity 950, sensor activation 955, and device power 960, and a speaker and related circuitry 965 for audible feedback.

As discussed further below, the patient 105 provides feedback to the SCS system 100, and specifically the CP 130, while the CP 130 establishes the program for the IPG 115. The patient 105 can activate the PFD 145 when the patient 105 feels various stimuli, such as paresthesia or pain.

Other means can be used for receiving patient feedback. For example, a patient can provide feedback using a mouth-piece that is inserted into the mouth of the patient, where the mouth-piece enables the user to provide feedback by biting the mouthpiece. Additionally, a patient can use an optical sensor (such as a camera and related image processing software) that detects visual cues from a patient, such as blinking of the patient's eyes, and/or a foot pedal that receives input by the patient manipulating a switch with his foot. It is also envisioned that the patient may provide feedback directly through the touch screen or hard buttons on the CP 130.

As discussed earlier, it should be understood that aspects of the SCS system 100 can be applied to other types of electrical stimulation systems. That is, other electrical stimulation systems provide electrical stimuli to other types of target tissues. Similar to the SCS system 100, these other electrical stimulation systems include one or more medical electrical leads having electrodes, a stimulation generator coupled to the one or more medical electrical leads, and a clinician programmer for establishing a program with the stimulation generator.

Figure 5:
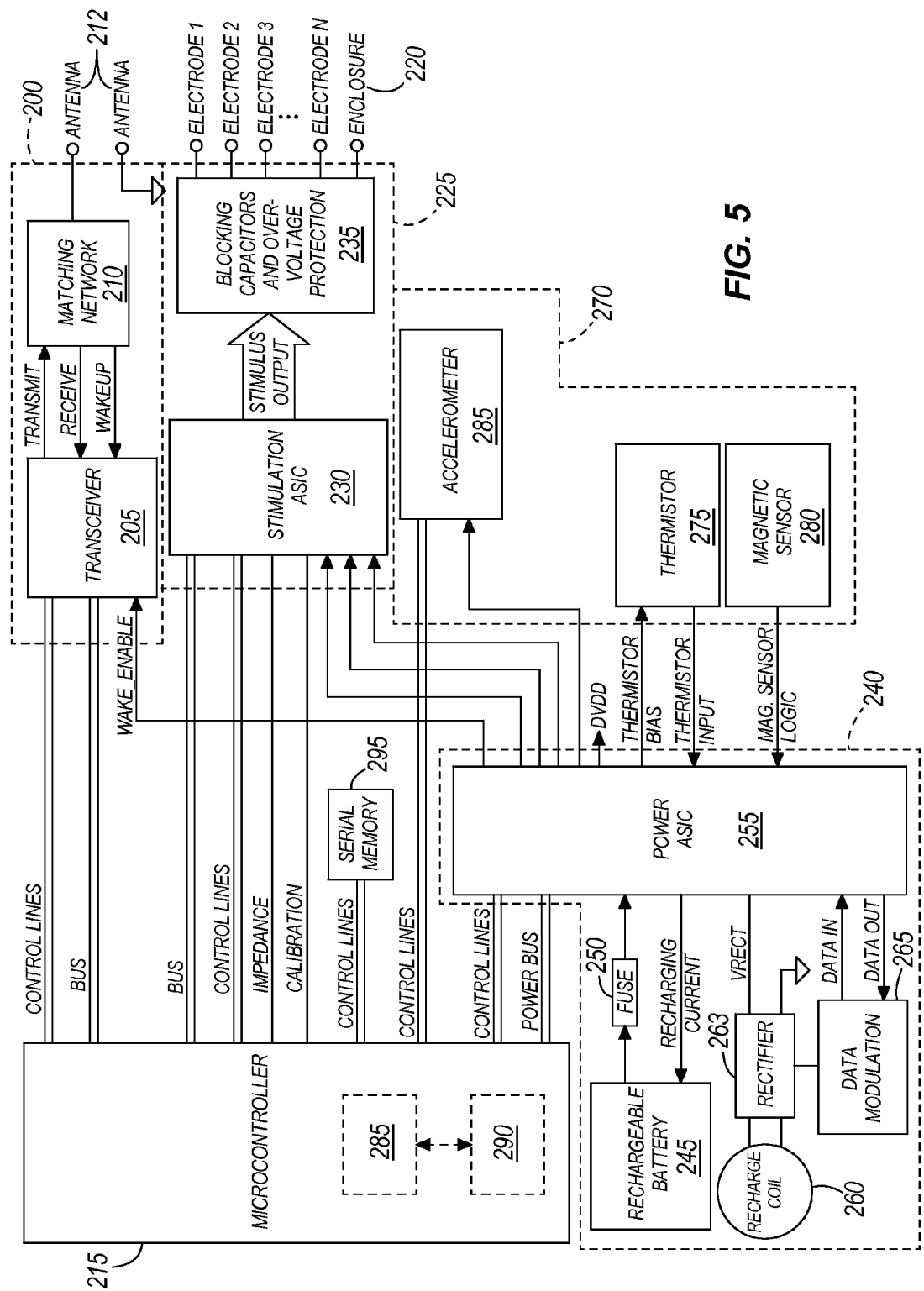
FIG. 5 is a block diagram of an implantable pulse generator for use in the spinal cord stimulation system of FIG. 1.

FIG. 5 shows a block diagram of one construction of the IPG 115. The IPG 115 includes a printed circuit board ("PCB") that is populated with a plurality of electrical and electronic components that provide power, operational control, and protection to the IPG 115. With reference to FIG. 5, the IPG 115 includes a communication portion 200 (also referred to as a communication unit) having a transceiver 205, a matching network 210, and antenna 212. The communication portion 200 receives power from a power ASIC (discussed below), and communicates information to/from the microcontroller 215 and a device (e.g., the CP 130) external to the IPG 115. For example, the IPG 115 can provide bi-direction radio communication capabilities, including Medical Implant Communication Service (MICS) bi-direction radio communication following the MICS specification.

The IPG 115, as previously discussed, provides stimuli to electrodes 150 of an implanted medical electrical lead 110. As shown in FIG. 5, N electrodes are connected to the IPG 115. In addition, the enclosure or housing 220 of the IPG 115 can act as an electrode. The stimuli are provided by a stimulation portion 225 in response to commands from the microcontroller 215. The stimulation portion 225 includes a stimulation application specific integrated circuit (ASIC) 230 and circuitry including blocking capacitors and an over-voltage protection circuit. As is well known, an ASIC is an integrated circuit customized for a particular use, rather than for general purpose use. ASICs often include processors, memory blocks including ROM, RAM, EEPROM, Flash, etc. The stimulation ASIC 230 can include a processor, memory, and firmware for storing preset pulses and programs that can be selected via the microcontroller 215. The providing of the pulses to the electrodes 150 is controlled through the use of a waveform generator and amplitude multiplier of the stimulation ASIC 230, and the blocking capacitors and overvoltage protection circuitry of the stimulation portion 225, as is known in the art. The stimulation portion 225 of the IPG 115 receives power from the power ASIC (discussed below). The stimulation ASIC 230 also provides signals to the microcontroller 215. More specifically, the stimulation ASIC 230 can provide impedance values for the channels associated with the electrodes 150, and also communicate calibration information with the microcontroller 215 during calibration of the IPG 115.

The IPG 115 also includes a power supply portion 240. The power supply portion includes a rechargeable battery 245, fuse 250, power ASIC 255, recharge coil 260, rectifier 263 and data modulation circuit 265. The rechargeable battery 245 provides a power source for the power supply portion 240. The recharge coil 260 receives a wireless signal from the PPC 135. The wireless signal includes an energy that is converted and conditioned to a power signal by the rectifier 263. The power signal is provided to the rechargeable battery 245 via the power ASIC 255. The power ASIC 255 manages the power for the IPG 115. The power ASIC 255 provides one or more voltages to the other electrical and electronic circuits of the IPG 155. The data modulation circuit 265 controls the charging process.

The IPG also includes a magnetic sensor 280. The magnetic sensor 280 provides a "hard" switch upon sensing a magnet for a defined period. The signal from the magnetic sensor 280 can provide an override for the IPG 115 if a fault is occurring with the IPG 115 and is not responding to other controllers.

The IPG 115 is shown in FIG. 5 as having a microcontroller 215. Generally speaking, the microcontroller 215 is a controller for controlling the IPG 115. The microcontroller 215 includes a suitable programmable portion 285 (e.g., a microprocessor or a digital signal processor), a memory 290, and a bus or other communication lines. An exemplary microcontroller capable of being used with the IPG is a model MSP430 ultra-low power, mixed signal processor by Texas Instruments. More specifically, the MSP430 mixed signal processor has internal RAM and flash memories, an internal clock, and peripheral interface capabilities. Further information regarding the MSP 430 mixed signal processor can be found in, for example, the "MSP430G2x32, MSP430G2x02 MIXED SIGNAL MICROCONTROLLER" data sheet; dated December 2010, published by Texas Instruments at www.ti.com; the content of the data sheet being incorporated herein by reference.

The IPG 115 includes memory, which can be internal to the control device (such as memory 290), external to the control device (such as serial memory 295), or a combination of both. Exemplary memory include a read-only memory ("ROM"), a random access memory ("RAM"), an electrically erasable programmable read-only memory ("EEPROM"), a flash memory, a hard disk, or another suitable magnetic, optical, physical, or electronic memory device. The programmable portion 285 executes software that is capable of being stored in the RAM (e.g., during execution), the ROM (e.g., on a generally permanent basis), or another non-transitory computer readable medium such as another memory or a disc.

Software included in the implementation of the IPG 115 is stored in the memory 290. The software includes, for example, firmware, one or more applications, program data, one or more program modules, and other executable instructions. The programmable portion 285 is configured to retrieve from memory and execute, among other things, instructions related to the control processes and methods described below for the IPG 115. For example, the programmable portion 285 is configured to execute instructions retrieved from the memory 290 for sweeping the electrodes 150 in response to a signal from the CP 130.

The PCB also includes a plurality of additional passive and active components such as resistors, capacitors, inductors, integrated circuits, and amplifiers. These components are arranged and connected to provide a plurality of electrical functions to the PCB including, among other things, filtering, signal conditioning, or voltage regulation, as is commonly known.

Figure 6:
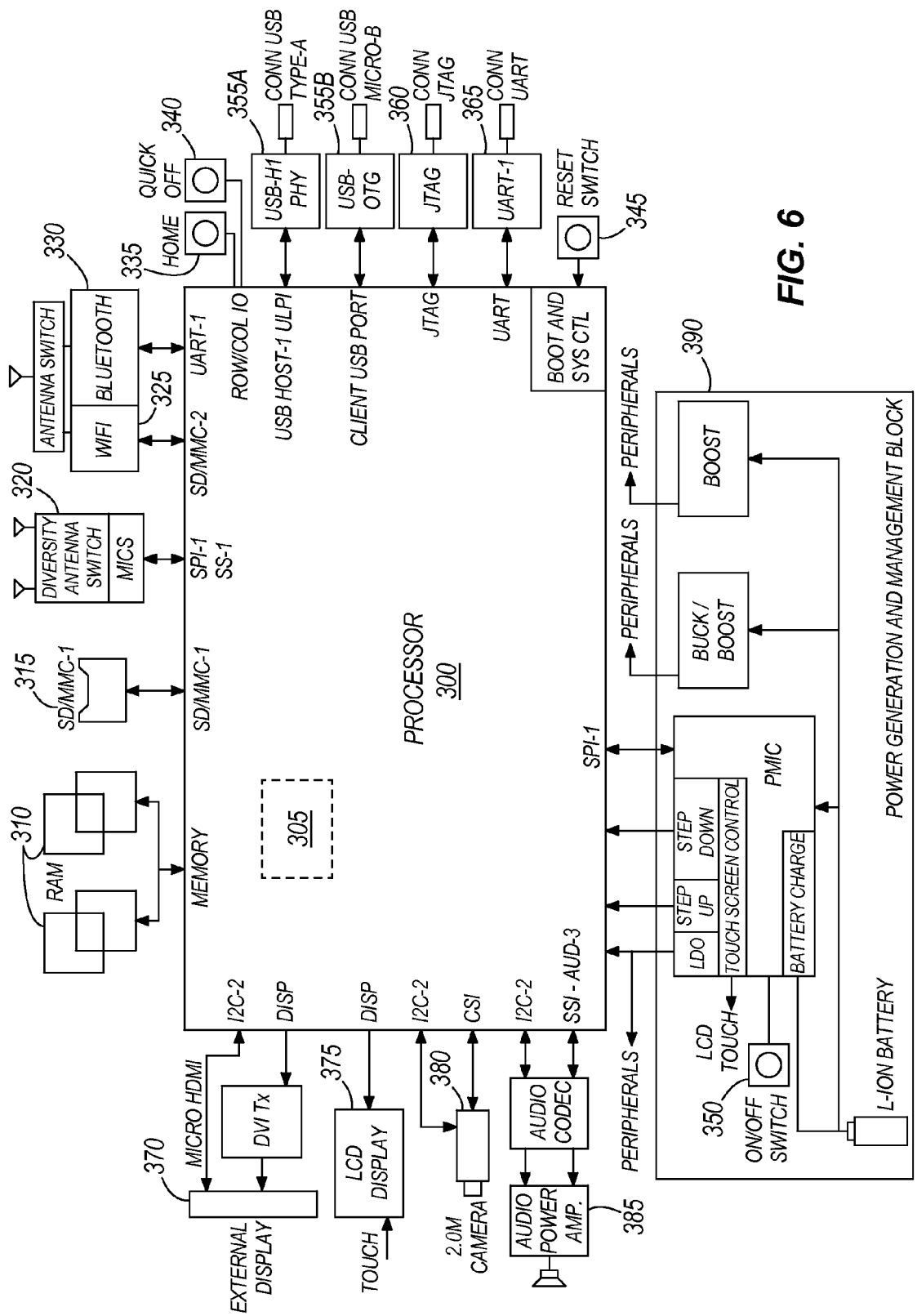
FIG. 6 is a block diagram of a clinician programmer for use in the spinal cord stimulation system of FIG. 1.

FIG. 6 shows a block diagram of one construction of the CP 130. The CP 130 includes a printed circuit board ("PCB") that is populated with a plurality of electrical and electronic components that provide power, operational control, and protection to the CP 130. With reference to FIG. 6, the CP includes a processor 300. The processor 300 is a controller for controlling the CP 130 and, indirectly, the IPG 115 as discussed further below. In one construction, the processor 300 is an applications processor model i.MX515 available from Freescale Semiconductor. More specifically, the i.MX515 applications processor has internal instruction and data caches, multimedia capabilities, external memory interfacing, and interfacing flexibility. Further information regarding the i.MX515 applications processor can be found in, for example, the "IMX51CEC, Rev. 4" data sheet; dated August 2010; published by Freescale Semiconductor at www.freescale.com, the content of the data sheet being incorporated herein by reference. Of course, other processing units, such as other microprocessors, microcontrollers, digital signal processors, etc., can be used in place of the processor 300.

The CP 130 includes memory, which can be internal to the processor 300 (e.g., memory 305), external to the processor 300 (e.g., RAM 310), or a combination of both. Exemplary memory include a read-only memory ("ROM"), a random access memory ("RAM"), an electrically erasable programmable read-only memory ("EEPROM"), a flash memory, a hard disk, or another suitable magnetic, optical, physical, or electronic memory device. The processor 300 executes software that is capable of being stored in the RAM (e.g., during execution), the ROM (e.g., on a generally permanent basis), or another non-transitory computer readable medium such as another memory or a disc. The CP 130 also includes input/output ("I/O") systems that include routines for transferring information between components within the processor 300 and other components of the CP 130 or external to the CP 130.

Software included in the implementation of the CP 130 is stored in the memory 305 of the processor 300, RAM 310, ROM 315, or external to the CP 130. The software includes, for example, firmware, one or more applications, program data, one or more program modules, and other executable instructions. The processor 300 is configured to retrieve from memory and execute, among other things, instructions related to the control processes and methods described below for the CP 130. For example, the processor 300 is configured to execute instructions retrieved from the memory 305, RAM 310, and/or ROM 315 for establishing a program to control the IPG 115.

One memory shown in FIG. 6 is RAM 310, which can be a double data rate (DDR2) synchronous dynamic random access memory (SDRAM) for storing data relating to and captured during the operation of the CP 130. In addition, a secure digital (SD) or multimedia card (MMC) can be coupled to the CP for transferring data from the CP to the memory card via slot 315. Of course, other types of data storage devices can be used in place of the data storage devices shown in FIG. 6.

The CP 130 includes multiple bi-directional radio communication capabilities. Specific wireless portions included with the CP 130 are a Medical Implant Communication Service (MICS) bi-direction radio communication portion 320, a WiFi bi-direction radio communication portion 325, and a Bluetooth bi-direction radio communication portion 330. The MICS portion 320 includes a MICS communication interface, an antenna switch, and a related antenna, all of which allows wireless communication using the MICS specification. The WiFi portion 325 and Bluetooth portion 330 include a WiFi communication interface, a Bluetooth communication interface, an antenna switch, and a related antenna all of which allows wireless communication following the WiFi Alliance standard and Bluetooth Special Interest Group standard. Of course, other wired, wireless local area network (WLAN) standards, and wireless personal area networks (WPAN) standards can be used with the CP 130.

The CP 130 includes three hard buttons: a "home" button 335 for returning the CP to a home screen for the device, a "quick off" button 340 for quickly deactivating stimulation IPG, and a "reset" button 345 for rebooting the CP 130. The CP 130 also includes an "ON/OFF" switch 350, which is part of the power generation and management block (discussed below).

The CP 130 includes multiple communication portions for wired communication. Exemplary circuitry and ports for receiving a wired connector include a portion and related port for supporting universal serial bus (USB) connectivity 355, including a Type-A port and a Micro-B port; a portion and related port for supporting Joint Test Action Group (JTAG) connectivity 360, and a portion and related port for supporting universal asynchronous receiver/transmitter (UART) connectivity 365. Of course, other wired communication standards and connectivity can be used with or in place of the types shown in FIG. 6.

Another device connectable to the CP 130, and therefore supported by the CP 130, is an external display. The connection to the external display can be made via a micro High-Definition Multimedia Interface (HDMI) 370, which provides a compact audio/video interface for transmitting uncompressed digital data to the external display. The use of the HDMI connection 370 allows the CP 130 to transmit video (and audio) communication to an external display. Of course other connection schemes, such as DVI, can be used with the CP 130.

The CP 130 includes a touch screen I/O device 375 for providing a user interface with the clinician. The touch screen display 375 can be a liquid crystal display (LCD) having a resistive, capacitive, or similar touch-screen technology. It is envisioned that multitouch capabilities can be used with the touch screen display 375 depending on the type of technology used.

The CP 130 includes a camera 380 allowing the device to take pictures or video. The resulting image files can be used to document a procedure or an aspect of the procedure. For example, the camera 380 can be used to take pictures of barcodes associated with the IPG 115 or the leads 110, or documenting an aspect of the procedure, such as the positioning of the leads. Similarly, it is envisioned that the CP 130 can communicate with a fluoroscope or similar device to provide further documentation of the procedure. Other devices can be coupled to the CP 130 to provide further information, such as scanners or RFID detection. Similarly, the CP 130 includes an audio portion 385 having an audio codec circuit, audio power amplifier, and related speaker for providing audio communication to the user, such as the clinician or the surgeon.

The CP 130 further includes a power generation and management block 390. The power block 390 has a power source (e.g., a lithium-ion battery) and a power supply for providing multiple power voltages to the processor, LCD touch screen, and peripherals.

As best shown in FIG. 1, the CP 130 is a handheld computing tablet with touch screen capabilities. The tablet is a portable personal computer with a touch screen, which is typically the primary input device. However, an external keyboard or mouse can be attached to the CP 130. The tablet allows for mobile functionality not associated with even typical laptop personal computers, which can be used in some embodiments of the invention.

In operation, the IPG 115 (or the EPG 115A) through the use of the implanted medical electrical leads 110, and specifically the electrodes 150, stimulates neurons of the spinal cord. The IPG 115 selects an electrode stimulating configuration, selects a stimulation waveform, regulates the amplitude of the electrical stimulation, controls the width and frequency of electrical pulses, and selects cathodic or anodic stimulation. This is accomplished by a healthcare professional (e.g., a clinician), using the CP 130, setting the parameters of the IPG 115. The setting of parameters of the IPG results in a "program" for the electrode stimulation. Programming may result in multiple programs that the patient can choose from. Having multiple programs allows, for example, the patient to find a best setting for paresthesia at a particular time of treatment.

With reference to FIG. 3, an electrode array 120 includes eight electrodes 150B. The shown electrode array 120 has two columns and four rows as viewed along a longitude length of the lead 110. More generically, the lead includes cl columns and r rows, where cl is two and r is four. When referring to a particular column, the column is referred to herein as the j-th column, and when referring to a particular row, the row is referred to as the i-th row.

Before proceeding further, it should be understood that not all electrode arrays 120 are conveniently shaped as a simple matrix having definite columns and definite rows. More complex configurations are possible, which are referred to herein as complex electrode array configurations. The processes discussed herein can account for complex electrode array configurations. For example, a representative array having cl columns and r rows for a complex electrode array configuration may include "dummy" addresses having "null" values in the array. For a specific example, an electrode contact may span multiple columns. The resulting array may have a first address i, j representing the multiple column electrode and a second address i, j+1 having a "null" value to account for the multiple columns of the multiple column electrode. This concept can be expanded to even more complex arrangements. Accordingly, all electrode arrays 120 can be addressed as a matrix and it will be assumed in the discussion below that the electrode array 120 has been addressed as a matrix.

Figure 7:
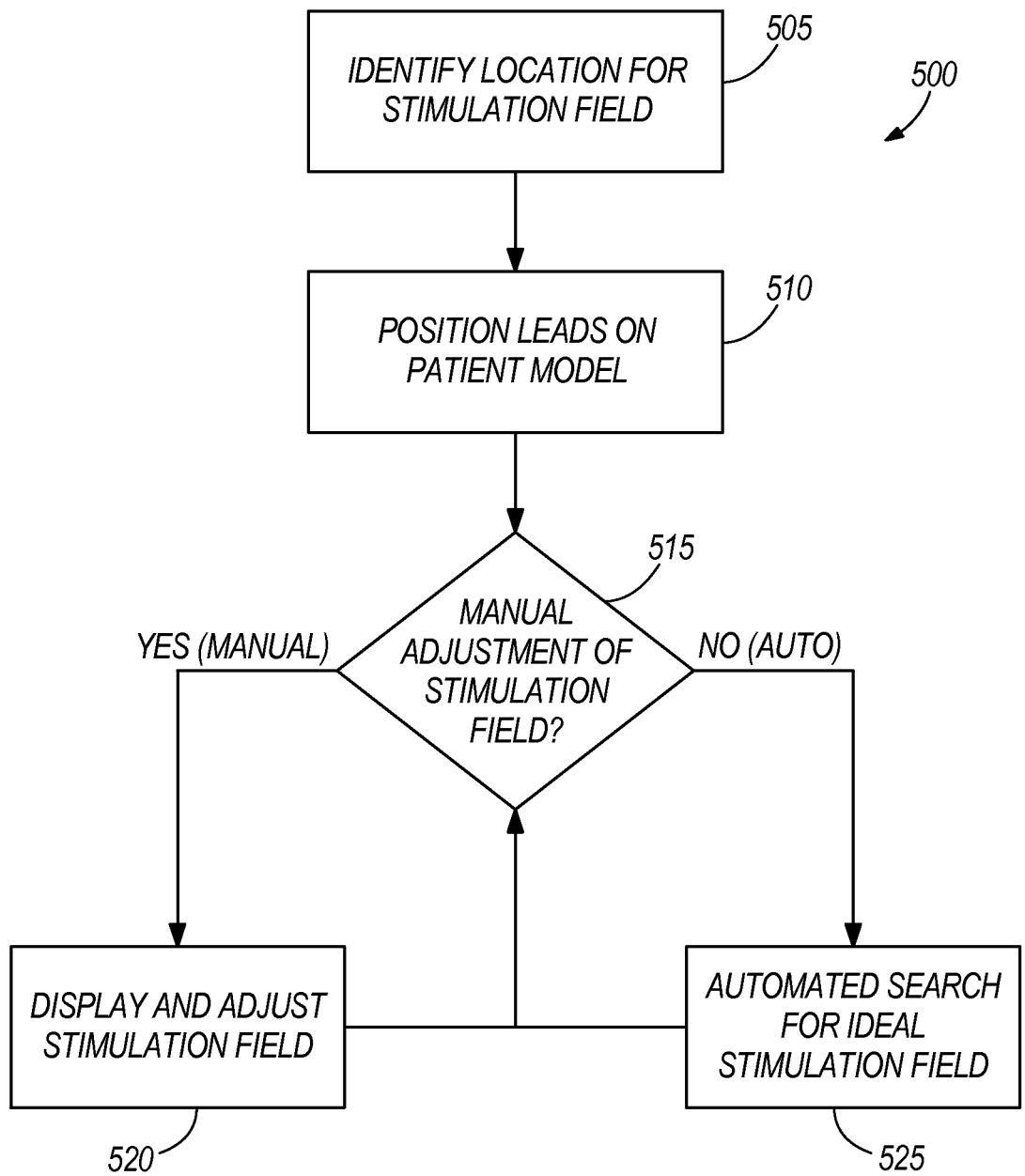
FIG. 7 is a flow diagram for providing electrical stimulation to a patient.

FIG. 7 illustrates a method 500 of providing electrical stimulation to a patient using, for example, the spinal cord stimulation system 100 described above. The method 500 begins with identifying a location on the spinal column of the patient 105 to receive stimulation (step 505). In step 510, the location of medical leads 110 implanted in the patient 105 is determined and positioned on a patient model displayed on a graphical user interface (GUI) (e.g., on display 375 of CP 130). In step 515, a user selects whether to proceed with manual configuration of the stimulation (step 520) or with an automated search for identify preferred stimulation programming (step 525). After proceeding with steps 520 and 525, the user may return to step 515.

Figure 11:
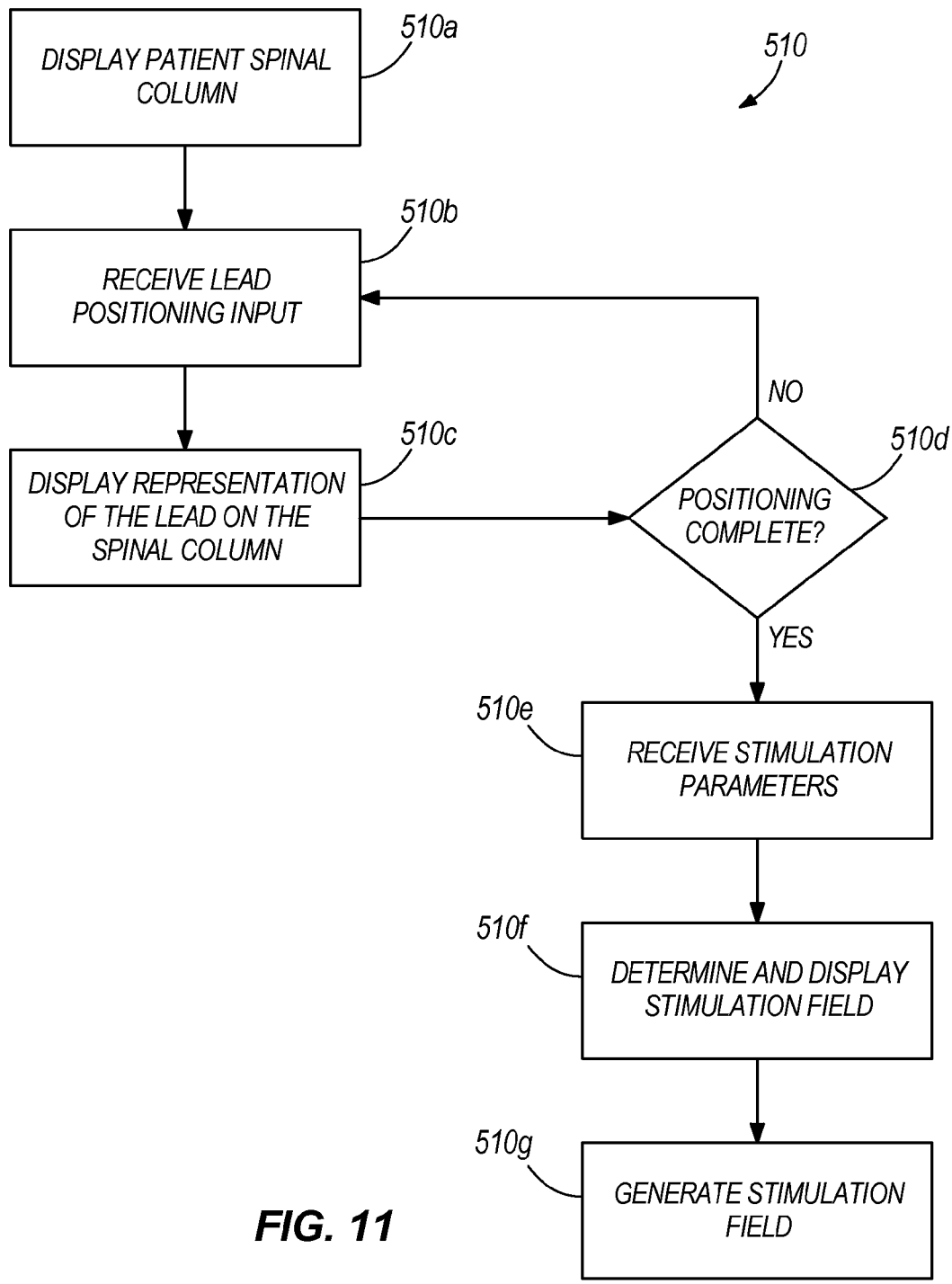
FIG. 11 is a flow diagram for positioning medical leads on a patient and modeling a stimulation field.
Figure 15:
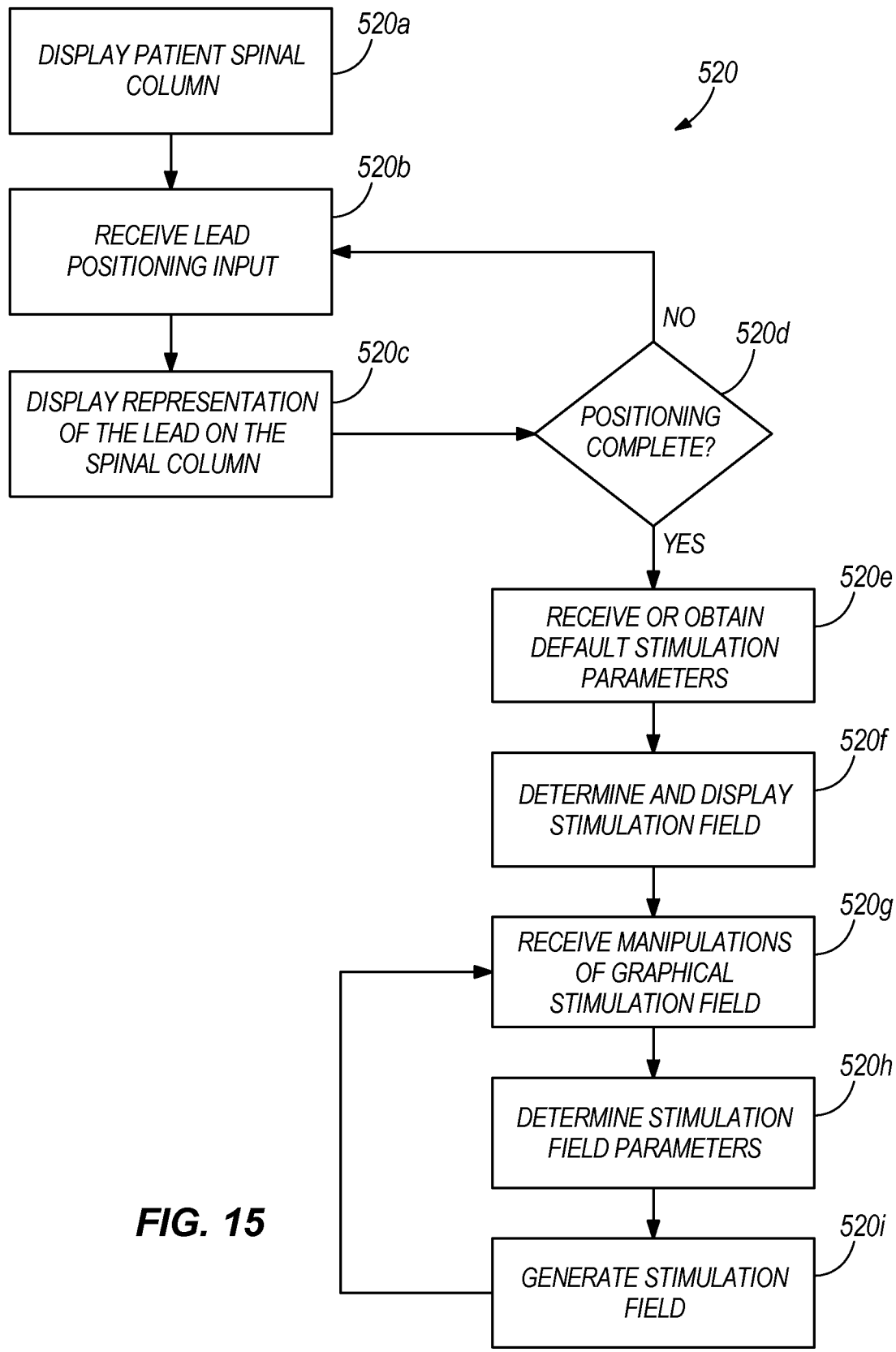
FIG. 15 is a flow diagram for manual programming with a graphical user interface.
Figure 17:
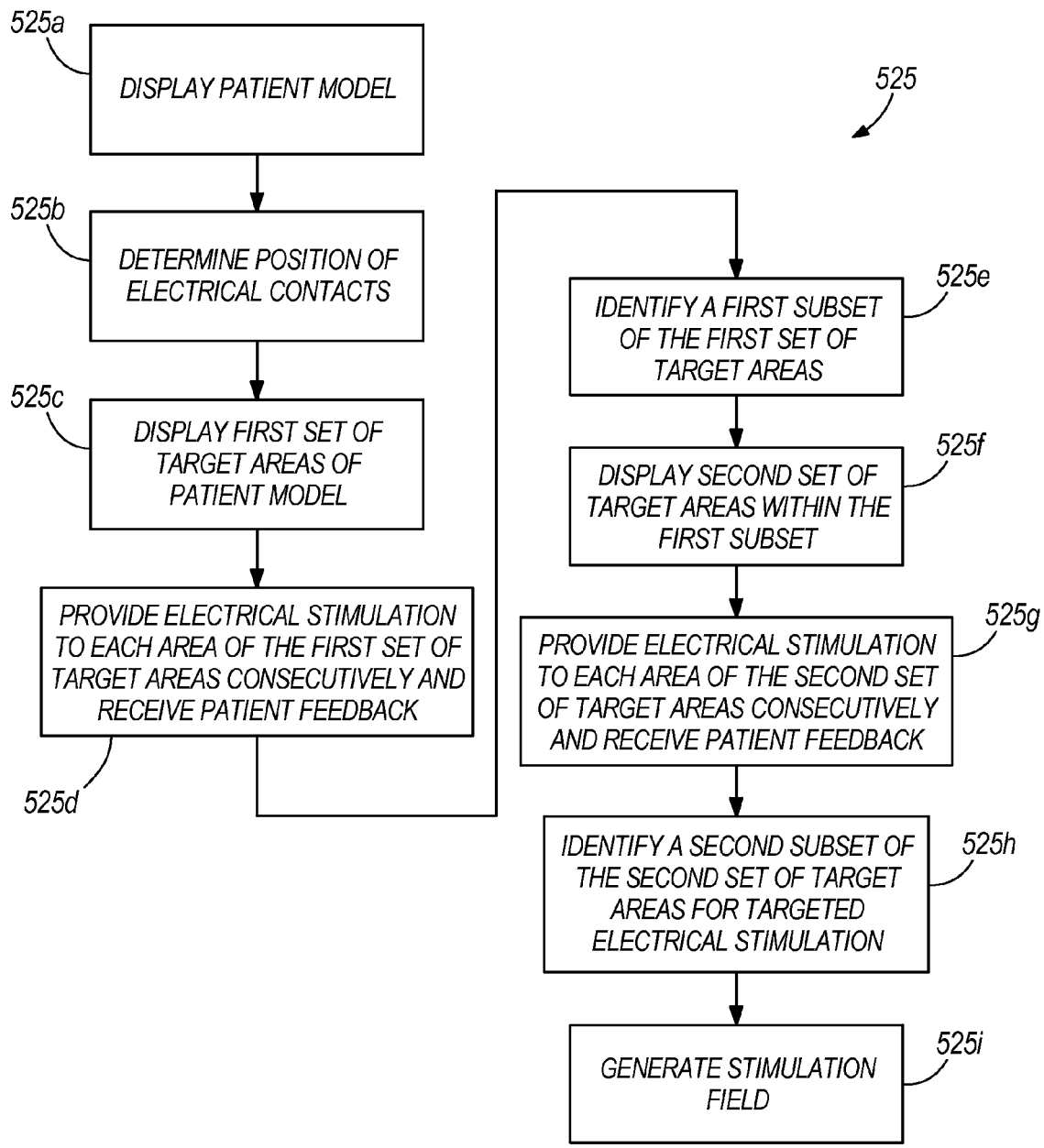
FIG. 17 is a flow diagram for automated programming with a graphical user interface.

Before proceeding further, it should be understood that the steps discussed in connection with FIG. 7 above and with FIGS. 8, 11, 15, and 17 below will be discussed in a generally iterative manner for descriptive purposes. However, various steps described herein with respect to the process of FIGS. 8, 11, 15, and 17 are capable of being executed simultaneously or in an order that differs from the illustrated serial and iterative manner of discussion. It is also envisioned that not all steps are required as described below. For instance, each of the steps of method 500 may be implemented alone, in combination with other steps, or in a different order than set forth in FIG. 7. As shown in FIG. 7, methods 510, 520, and method 525 may be carried out in series. However, the methods 510, 520, and 525 are shown in FIGS. 11, 15, and 17, respectively, to include steps that are nearly duplicative to one another. For example, steps 510a to 510f are similar to steps 520a to 520f. Thus, if method 510 as shown in FIG. 11 were executed first, then method 520 as shown in FIG. 15, steps 510a to 510f would, in essence, be executed a second time when steps 520a and 520f are performed. The methods are illustrated in this manner to highlight the independence of methods 510, 520, and 525. However, when carrying out methods 510, 520, and 525 in series as shown in FIG. 7, at least in some instances, such repetitive steps are not re-executed. For example, in executing the methods 510 and 520 in series, as shown in FIG. 7, at least in some instances, either steps 510a to 510f or steps 520a to 520f, but not both, are executed.

Figure 8:
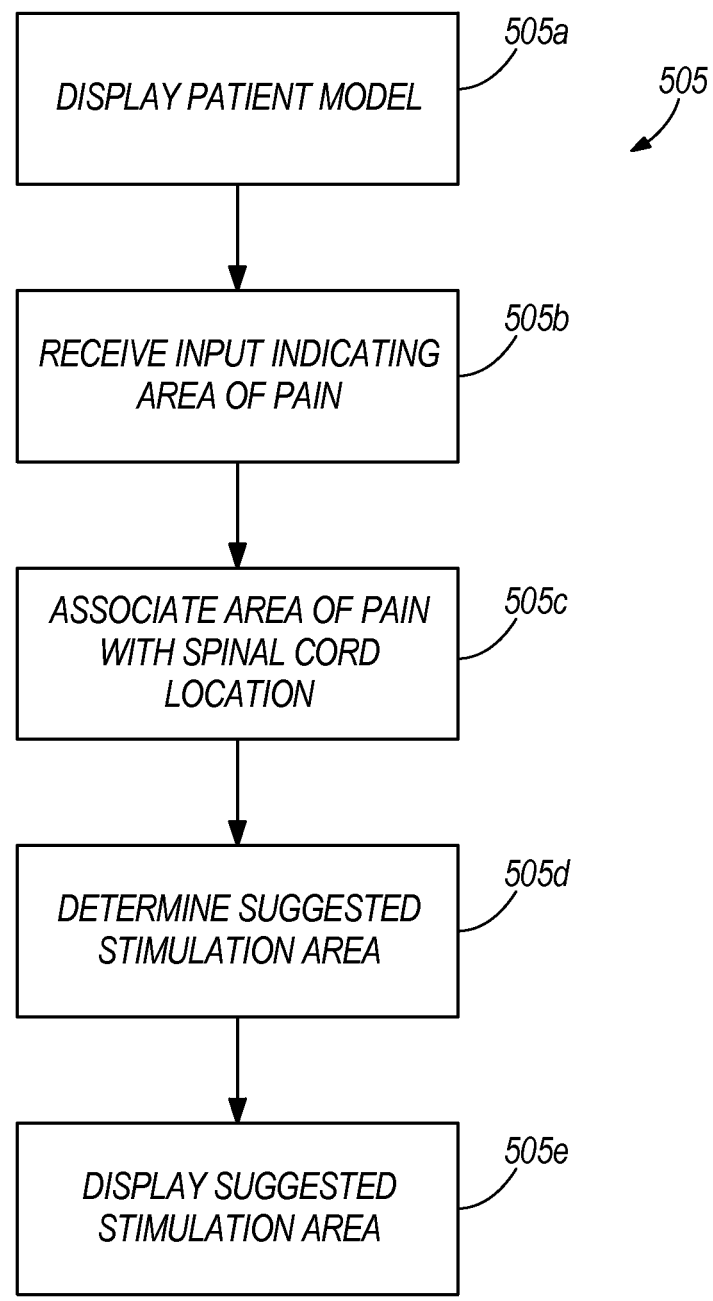
FIG. 8 is a flow diagram for identifying a location for receiving electrical stimulation.
Figure 9C:
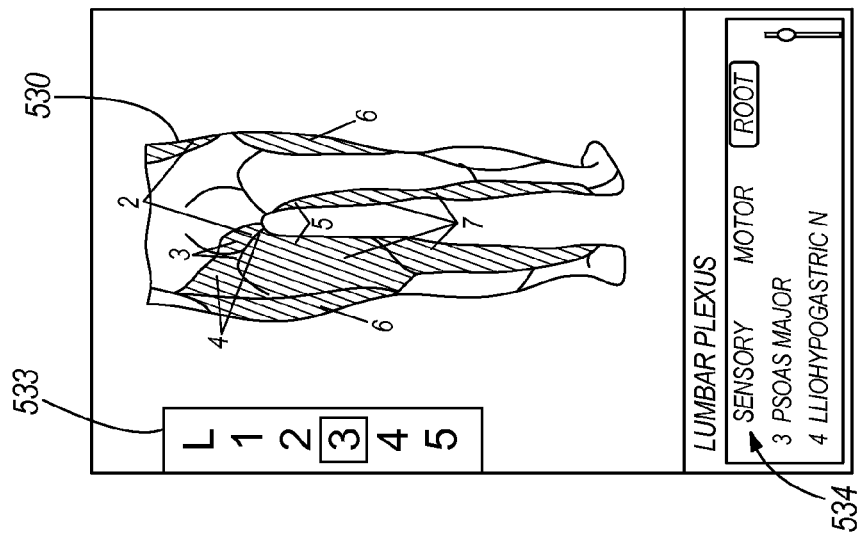
FIGS. 9A-C illustrate a graphical user interface for identifying a location for receiving electrical stimulation.
Figure 9B:
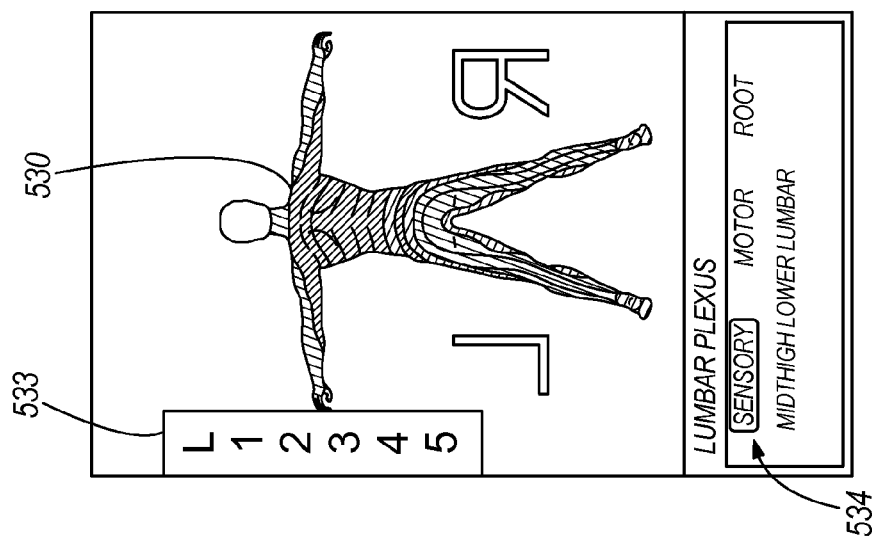
Figure 9A:
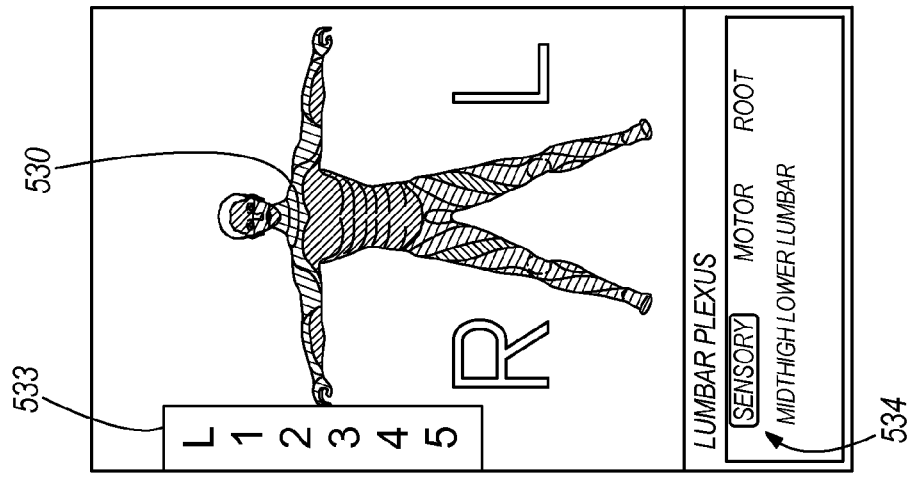

FIG. 8 illustrates step 505 (also referred to as method 505) in greater detail. In step 505a, a patient model is displayed on a display device. For instance, an image of a human may be shown on the touch screen display 375 of the CP 130. The user (e.g., the patient 105 or another on behalf of the patient) may request alternate views of the patient model 530, such as a front or back view as illustrated in FIGS. 9A and 9B, respectively. Additionally, the patient may magnify various portions of the patient model 530 to view the portion in more detail. FIGS. 9A-C depict various views of a patient model 530 as displayed on touch screen display 375 including a front, back, and magnified view.

In step 505b, the user selects an area on the patient model 530 that corresponds to an area of pain on the patient 105. The user may make the selection via the touch screen capabilities of the touch screen display 375, or another user input of the CP 130 (e.g., mouse, keyboard, etc.). The user may more generally select an area on the patient model 530 to request a magnified view (e.g., FIG. 9C) and, thereafter, indicate the location of pain on the patient model 530 more particularly.

Upon receiving the user indication of the area of pain on the patient model 530, the CP 130 associates the area of pain with a spinal column location in step 505c. For instance, the CP 130 accesses a database that receives as input a body part location and returns as output an associated spinal column location. The database may be stored locally (e.g., in memory 305) or remotely (e.g., accessible via an Internet or local network connection). For instance, in FIGS. 9A and 9B, in response to user input selecting the mid-thigh of the right leg of the patient model 530, the CP 130 associates the selection with the L3 vertebrae and the lumbar plexus. The CP 130 may also indicate the association in step 505c by, e.g., a textual or image output. Additionally, the user may specify the type of nerves being listed or highlighted. For instance, in response to the user selecting one of a sensory, motor, and root graphical buttons 534, the CP 130 lists and/or highlights on the patient model 530 the sensory, motor, and root nerves, respectively, associated with the area of pain indicated by the user input. In some instances, the CP 130 includes a representation of the spinal column 533 that can be used to highlight the associated location on the spinal column determined in step 505c.

In step 505d, the CP 130 determines a suggested stimulation area to stimulate the associated spinal column location. A database may store suggested stimulation areas such that the database receives as input a spinal column location and provides as output the suggested stimulation area. The database may be the same database referred to with respect to step 505c. In some embodiments, steps 505c and 505d are combined into a single step. In other words, an identified pain location is input to the CP 130 and the CP 130 determines a suggested stimulation area without first associating the pain area with a spinal column location. The steps of associating may be performed by an association module (not shown) of the CP 130.

Figure 10:
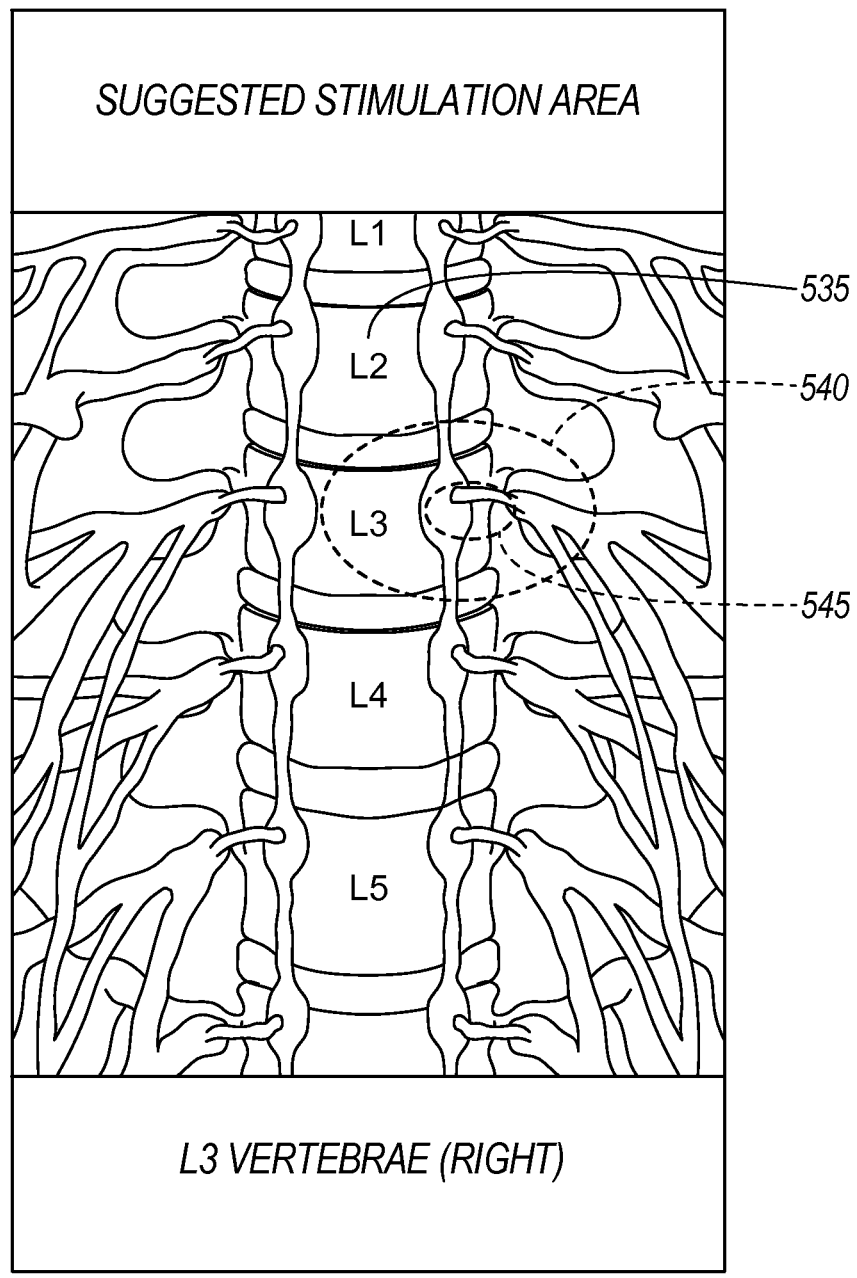
FIG. 10 illustrates a graphical user interface that displays a location for receiving electrical stimulation.

In step 505e, the determined stimulation area is displayed to the user and/or patient. For instance, FIG. 10 depicts an anatomically correct spinal column 535 representation of the patient and a suggested stimulation field 540 including a target area 545 near the L3 vertebrae. The term "anatomically correct" means a generally realistic representation of the particular patient's anatomy or an actual image (e.g., x-ray image) of the patient, rather than a generic image applicable to patients with significantly different anatomies. Thus, an anatomically correct image is scaled to a patient to accommodate differently sized patients or is otherwise customized to a particular patient or to particular characteristics associated with the patient.

Although method 505 is discussed as being implemented using the CP 130, another computer device, such as a personal computer, laptop, tablet, smart phone, etc., may be used in method 505 either in place of or in combination with the CP 130. For instance, the CP 130 may transmit user input to another computer device for remote computing or the CP 130 may access information remotely stored on another computer device to execute method 505.

FIG. 11 illustrates step 510 (also referred to as method 510) for modeling the position of one or more medical leads 110 (e.g., graphical leads 575a and 575b) on a patient model in greater detail. The position of one or more medical leads 110 are modeled based on actual medical leads 110 implanted within the patient 105. Accurately modeling the actual placement of the medical leads 110 within the patient 105 assists a user in stimulation programming. With the input of stimulation parameters, the method 510 also enables modeling of stimulation generated by the medical leads 110. This modeling further assists a user in stimulation programming. Additionally, the method 510 allows a user to model medical leads 110 and stimulation before actually implanting the medical leads 110 within the patient 105. In turn, the method 510 assists a clinician in determining where to position leads 110 within the patient 105 to obtain desired stimulation. It is also envisioned that position modeling can be extended to other portions of the stimulation system, such as the IPG 115 for example.

The method 510 begins in step 510a with displaying an image of a spinal column 560 as shown in FIG. 12A. For instance, the spinal column 560 may be displayed on the display 375 of the CP 130. The user may specify patient information, such as height, weight, etc., such that the image of the spinal column 560 is scaled to be anatomically correct. Alternatively, the image of the spinal column 560 may be an actual fluoroscope or x-ray image received by the CP 130. For instance, the user may take a picture of an x-ray with the camera 380 of the CP 130, or the CP 130 may communicate with a fluoroscope or similar device to receive the image of the spinal column 560. The CP 130 may further include image processing to convert the image into an appropriate format, to suppress unwanted details, to highlight desired aspects, or otherwise ready the image for display on the CP 130.

In step 510b, the user inputs lead positioning input. The user first selects one or more lead types to be positioned on the patient model. The selected leads should generally represent the leads 110 already implanted in the patient 105 or leads that may potentially be implanted within the patient 105. For example, the user may select one or more leads representing the in-line lead 110A (FIG. 2), the paddle lead 110B (FIG. 3), or another medical lead type.

Figure 12E:
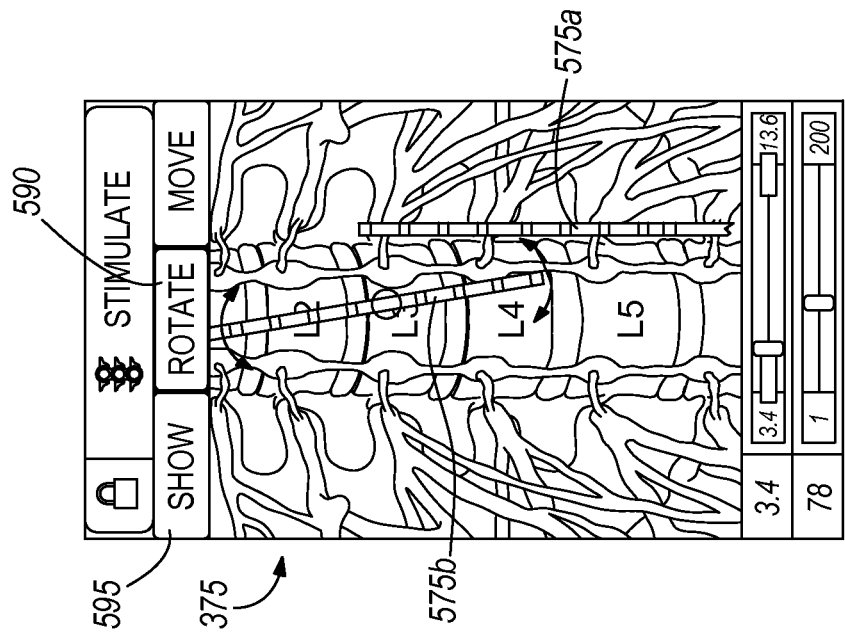
Figure 12D:
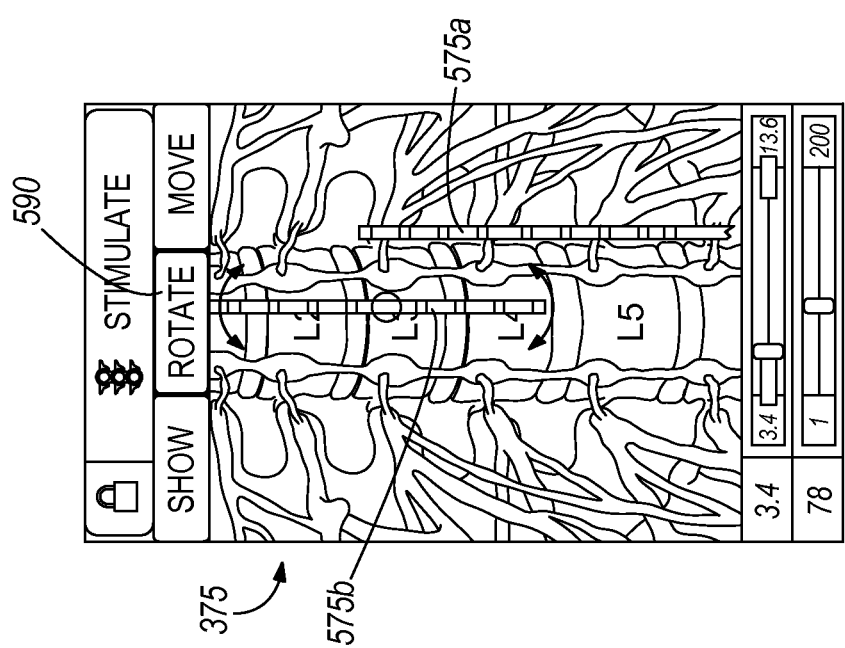

Once the one or more leads are selected, in step 510c, they are overlaid on the image of the spinal column 560, as shown in FIG. 12B. In the FIG. 12B example, the user has selected two in-line type leads (representing in-line leads 110A), which are shown as leads 575a and 575b. In step 510d, the user indicates whether he or she has completed positioning the selected medical leads. If not, the method returns to step 510b to receive additional user input. In FIGS. 12A-E, the user is able to "move" or "rotate" the leads 575a and 575b to position the lead on the spinal column 560. For instance, using the touch screen display 375 or other input devices, the user is able to select a graphical lead and to cause its movement or rotation on the display 375. The move button 585 and rotate button 590 alter the positioning action that the user may cause with respect to the graphical lead. As shown in FIG. 12B and FIG. 12C, with the move button 585 selected, the user moves the selected lead 575b upwards. In FIGS. 12D and 12E, with the rotate button 590 selected, the user rotates the selected lead 575b counter-clockwise. Additionally, the user may alter the size of the leads 575a and 575b by dragging the boundaries of the lead via the touch screen display 375 or other input device. In some instances, an additional "resize" graphic button, similar to the move button 585 and rotate button 590, is shown on the display 375 such that the user can selectively enable/disable the ability to resize the leads 575a and 575b. Thus, the user is able to provide the CP 130 with positioning input to position the leads 575a and 575b in the anatomically correct position (e.g., the lead 575b is generally in the middle of the spinal column 560 along the L2, L3, and L4 vertebrae), in the anatomically correct orientation (e.g., the lead 575b is rotated slightly counterclockwise), and with the anatomically correct size (e.g., the lead 575a and 575b are the appropriate scale/size relative to the spinal column 560).

In some instances, when an actual image of the patient, such as an x-ray or fluoroscope image, is received by the CP 130 in step 510a, the CP 130 may use image processing in step 510b to analyze the received image to identify the actual lead position, orientation, and size. The positioning input of the leads is received from an image processing module (not shown) of the CP 130. Thereafter, in step 510c, the spinal column 560 and leads 575a and 575b, as identified, are displayed on the screen 375. The user may still adjust the position of the leads 575a and 575b by cycling through steps 510d, 510b, and 510c as necessary. Additionally, the user may specify to the CP 130 the lead type(s) in step 510b, particularly if the CP 130 is not able to deduce the type based on the positioning input.

Figure 12F:
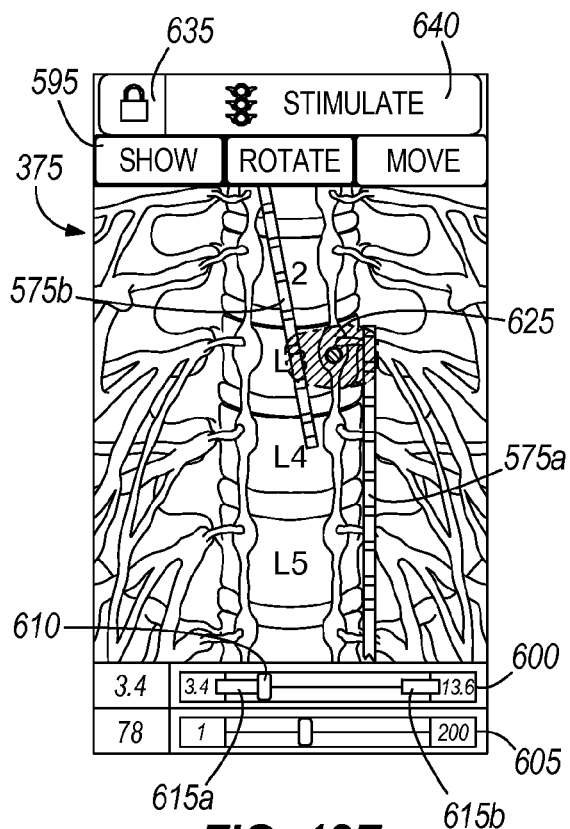
Figure 12G:
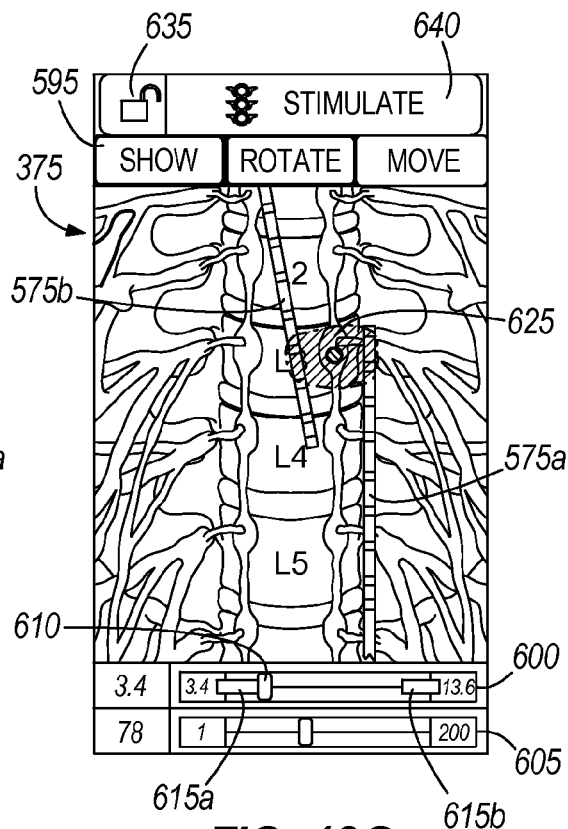
Figure 12H:
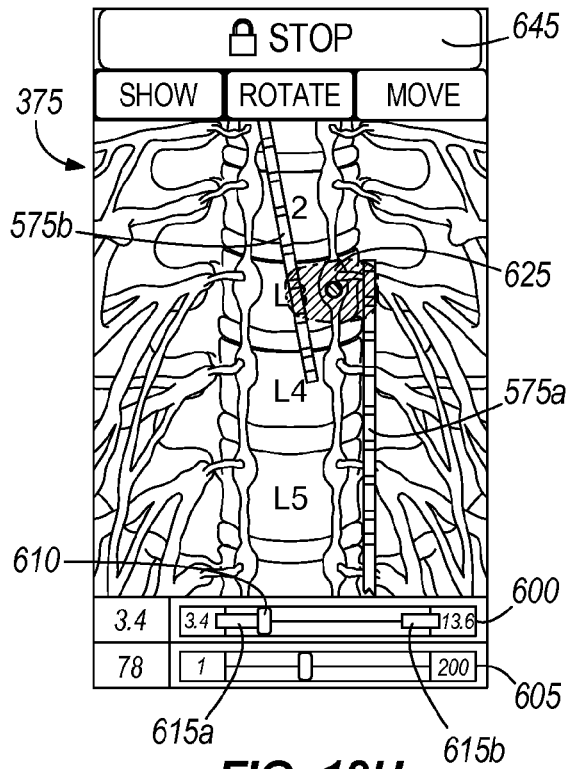
Figure 12I:
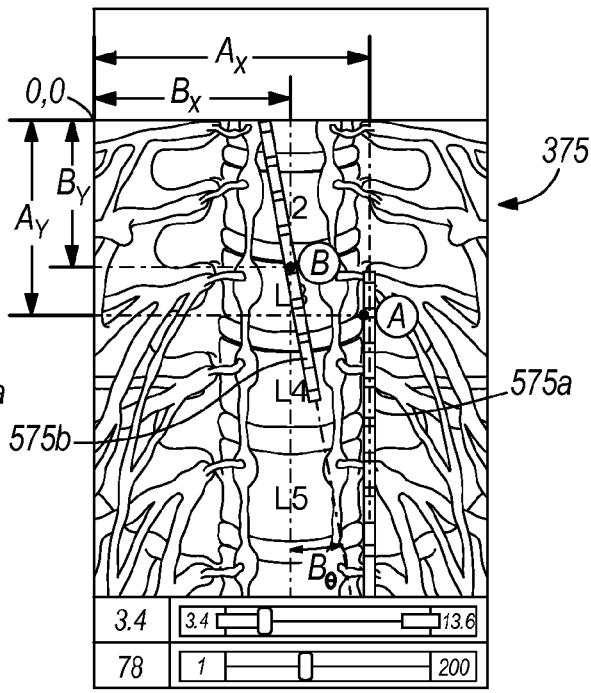

To indicate that the user has completed positioning the leads 575a and 575b, the user may select the show button 595. The user may return to further modify the lead positions by again de-selecting the show button 595. Other user actions may be used to indicate completion of lead positioning as well. The positions of the leads 575a and 575b may be transmitted and stored within the IPG 115 for later retrieval. The positions of the leads 575a and 575b may be represented using coordinates in an x-y coordinate system overlaid on the screen 375. For instance, FIG. 12I depicts x-y coordinates and an angle ($A_X$, $A_Y$, $A_\theta$) for lead 575a and ($B_X$, $B_Y$, $B_\theta$) for lead 575b, with the origin (0,0) positioned in the upper left portion of the screen 375. The x-y-angle coordinates ($A_X$, $A_Y$, $A_\theta$) and ($B_X$, $B_Y$, $B_\theta$) indicate, respectively, the location of a reference point on the leads 575a and 575b, and an angle of an axis of the leads with respect to a vertical line (parallel with the y-axis) passing through the x-position of the reference point. The reference point may be, for instance, an electrode, a mid-point, an end-point, or another portion of the lead. Additionally, in some instances, multiple coordinates for each lead 575a and 575b are provided to indicate multiple reference points (e.g., electrodes) of the leads 575a and 575b. The locations of electrodes that were not specified by the coordinates can be deduced based on the position data (x-y-angle coordinates) received and based on knowledge of the particular lead type. Having the particular electrode locations allows the CP 130 to be aware of relative positions of the electrodes, which assists in modeling stimulation and determining desired stimulation parameters. Additional or alternative positioning information of the leads 575a and 575b may include the size of the leads (length, wide, height), number of electrodes, electrode positions along the leads, among other information.

Also transmitted to the IPG 115 can be an identifier for the spinal column representation used in the original positioning process or the image actually used in the positioning process. For example, the identifier can identify which representation, image, model, or map originally used to generate the position data, thereby allowing better rendering upon later retrieval. If the patient 105 later returns to a clinician for additional programming, the IPG 115 implanted in the patient 105 may communicate the position data (including the image or identifier) to the second (or subsequent) CP 130 of the clinician for rendering. If an identifier is used, the second CP 130 can use the identifier to select the same image used in the original positioning process for the subsequent positioning process. Thus, the communication of position data can replace step 510b of method 510 and eliminate the need to cycle through steps 502b-520d, reducing the time needed for programming. The position data transferred to the second CP 130 can also assist in evaluating or performing a procedure on the patient 105. Moreover, the position data, even if just relational data, can be particularly useful when multiple leads are connected to the IPG 115. The position data allows for a better representation of the interacting stimulation fields when stimulating the electrodes of each lead.

Figure 13:
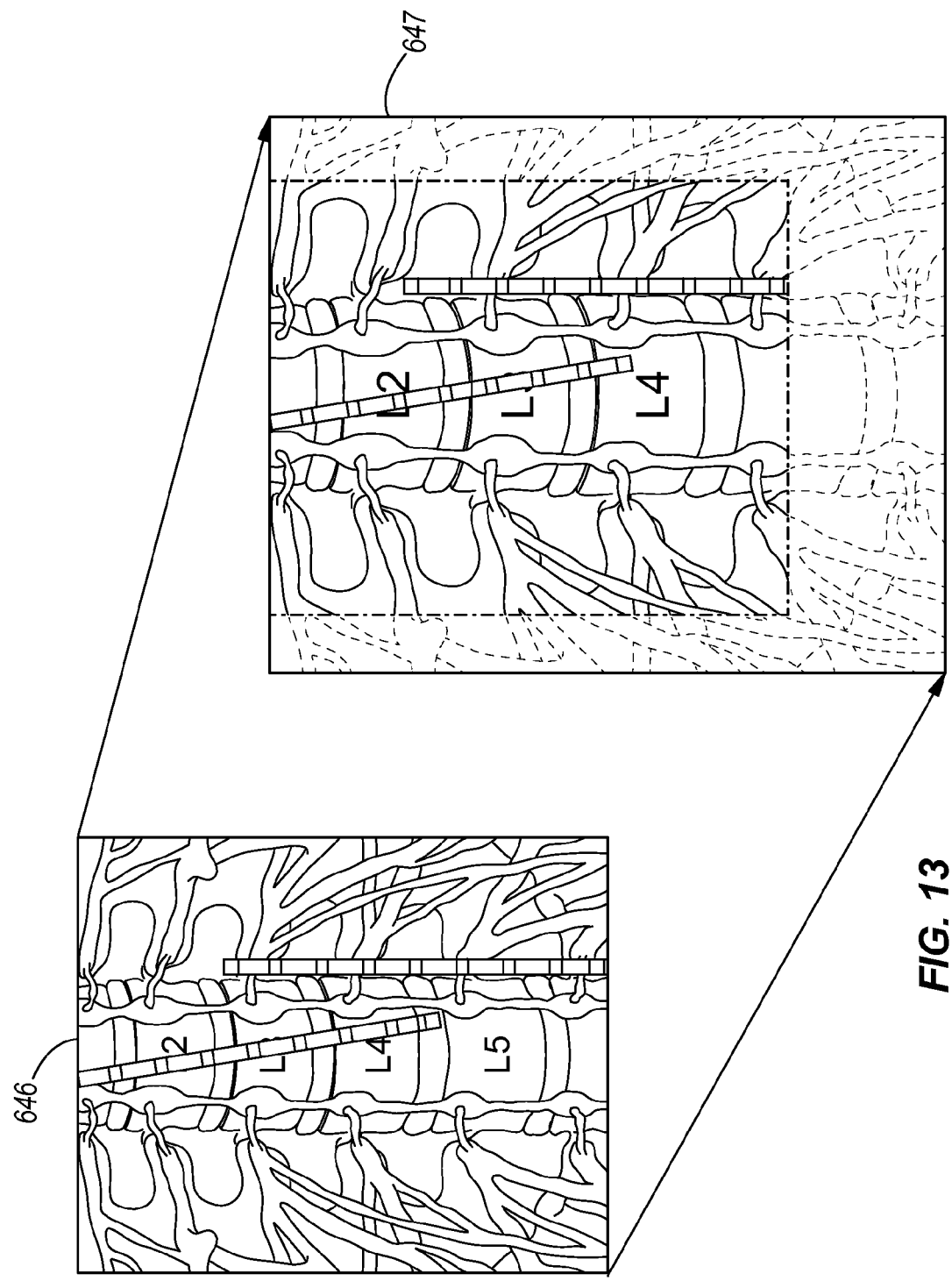
FIG. 13 illustrates an original image and a scaled image of a spinal column.

In some instances, a scaling parameter is sent along with the identifier of the spinal column representation or actual image used in the positioning process. Scaling an image enables a particular image to be used to represent patients of various sizes. For instance, FIG. 13 illustrates an original image 646 at 100% and a scaled image 647 at 125%. While the scaled image 647 is larger, a corresponding smaller area of the image is presented in the display 375 shown in the dashed rectangle) and the leads are not scaled. Alternatively, the scaling may be applied to the leads 575a and 575b instead of or in addition to the image to ensure proper proportional representation.

Figure 14:
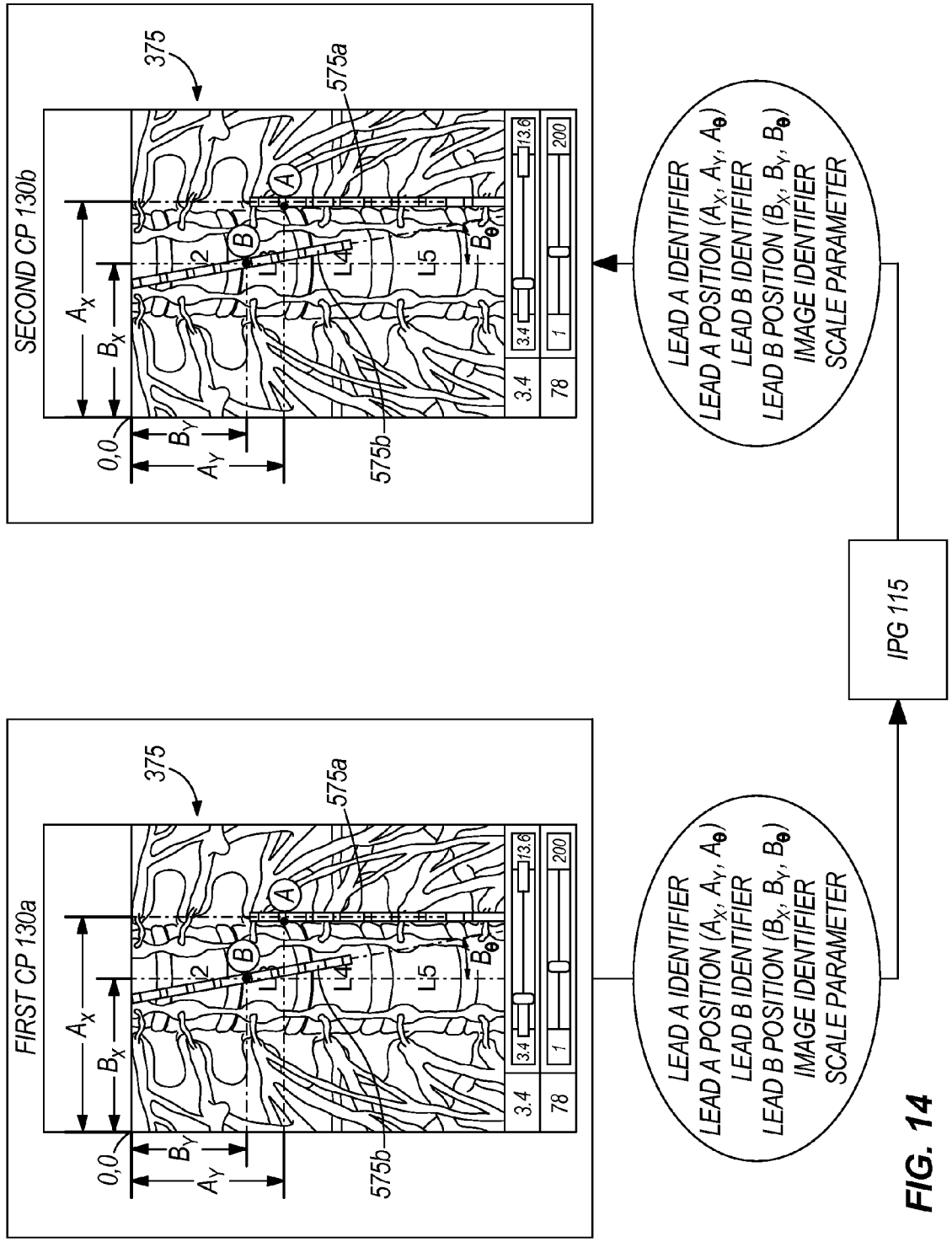
FIG. 14 illustrates the transmission of lead data and image data between a first programmer, an implanted pulse generator, and a second programmer.

FIG. 14 illustrates a first CP 130a storing lead position data and image data on the IPG 115, and a second CP 130b later retrieving the lead data and image data from the IPG 115. As described above, a first CP 130a is used for initial programming of the IPG 115. The initial programming includes storing lead data and image data on the IPG 115. The lead data includes a lead identifier and position information for each lead. The image data includes an image identifier and a scaling parameter. Subsequently, a second CP 130b may receive from the IPG 115 the stored lead data and image data. The second CP 130b may then select and retrieve a copy of the image from an accessible image database (whether local or remote) using the image identifier. The second CP 130b then scales and displays the image according to the scaling parameter. The second CP 130b then selects and retrieves graphics of the leads from an accessible lead database (whether local or remote) based on the lead identifiers, and overlays the graphics according to their respective lead position data. In some instances, the graphics of the leads may be scaled according to a lead scaling parameter provided in addition to or in place of the image scaling parameter. Thus, the second CP 130b has recreates the image and leads as they were displayed on the first CP 130a. Thereafter, the second CP 130b can perform additional programming of the leads.

Once the user has completed positioning the leads 575a and 575b as determined in step 510d, the user enters stimulation parameters for the leads 575a and 575b in step 510e. In step 510e, the user indicates which electrodes on the medical leads are to be activated and whether each is an anode or cathode. The user may make these indications via the touch screen display 375 or other input devices of the CP 130. For instance, the user may point to and select one or more electrodes to mark them for activation, and also indicate whether the electrode is an anode or cathode via other buttons of the user interface. Additionally, the user indicates the amplitude and pulse width for the electrical driving signals sent to the activated electrodes. FIG. 12F depicts an amplitude control 600 and a pulse width control 605, which each have a sliding tab 610 for the user to manipulate to indicate the desired amplitude and pulse width, respectively, for the selected lead. The control bars also have shutters 615 (left shutter 615a and right shutter 615b) that limit the minimum and maximum selectable amplitude and pulse width. The shutters 615 may be customized by the user or preprogrammed for a particular use, medical lead type, etc. In some instances, the amplitude and pulse width have default settings, such as the minimum potential amplitude and pulse width. The user may also program other stimulation parameters of leads 575a and 575b, such as frequency and pulse shape.

After the stimulation parameters are entered, in step 510f, an expected stimulation field 625, based on the entered parameters, is determined and displayed on the display 375. FIG. 12F depicts the expected stimulation field 625 as described in relation to step 510f. As the intensity of the expected stimulation field 625 is increased (e.g., the amplitude increased and the "on" duty cycle of the pulse width increased), the more opaque the expected stimulation field 625 appears. Other colors or graphic alterations to the expected stimulation field 625 may be used in some implementations. Additionally, the user may further adjust the stimulation parameters and view the changes to the expected stimulation field in real-time. In other words, steps 510e and 510f may be repeated as desired by the user.

In step 510g, the user causes generation of a stimulation field via the user interface of the CP 130. First, the user disables the stimulation lock button 635. Once the stimulation lock button 635 is disabled (see FIG. 12G), the user may enable the stimulate button 640. When the stimulate button 640 is enabled, a stop button 645 replaces both the stimulation lock button 635 and the stimulate button 640 on the display 375, and the expected stimulation field 625 (now representing actual stimulation) changes in appearance (e.g., it becomes more opaque), as shown in FIG. 12H. Additionally, when the stimulate button 640 is enabled, the IPG 115 generates stimulation of the spinal cord according to the input stimulation parameters. For instance, the CP 130 transfers the stimulation parameters and instructions to the IPG 115 via one of the various communications interfaces described above. Selecting the stop button 645 on the display 375 ceases the stimulation and re-enable the stimulation lock button 635 as shown in FIG. 12F.

FIG. 15 depicts a step 520 (also referred to as method 520) for receiving user input to modify a graphical depiction of a stimulation field via a graphical user interface to generate and manipulate an actual stimulation field. The method 520 begins with steps 520a, 520b, 520c, 520d, 520e, and 520f, which are similar to steps 510a, 510b, 510c, 510d, 510e, and 510f of method 510. Although the user inputs stimulation parameters in step 510e, default parameters may be used in place of or in combination with user input stimulation parameters in step 520e. Regardless, in step 520f, like 510f, a stimulation field 655 with target 660 resulting from the chosen or default stimulation parameters is displayed on the CP 130, along with a spinal column 560, as shown in FIG. 16A.

In step 520g, the user manipulates the stimulation field 655 and/or target 660. The user interface includes a shape button 670 and move button 675 to enable the user to specify the type of modification to the stimulation field 655 and/or target 660 that the user is able to perform. When the move button 675 is enabled, the user can move (pan) the entire stimulation field 655 and target 660 up, down, left, or right, either together or independently. For example, the user may drag the stimulation field 655 or target 660 (e.g., via a mouse or touch screen display 375 input) to move of the stimulation field 655 or target 660. When the shape button 670 is enabled, the user can modify the shape of the stimulation field 655 and target 660, together or independently. For example, the user may drag the boundaries of the stimulation field 655 or target 660 (e.g., via a mouse or touch screen display 375 input) to alter the shape of the stimulation field 655 or target 660. These shape and position modifications are graphical manipulations, in that they include a user inputting commands into a graphical user interface to adjust a graphic depiction of stimulation. The graphical manipulations are then translated by the programmer 130 into changes for the stimulation parameters of the electrode array 120 to generate the stimulation field 655 and target 660 as graphically depicted. Graphical manipulations contrast with, for instance, a user manually adjusting stimulation parameters, such as amplitude and pulse width, by entering or adjusting numeric values (e.g., using the amplitude control 600 or pulse width control 605).

Figure 16A:
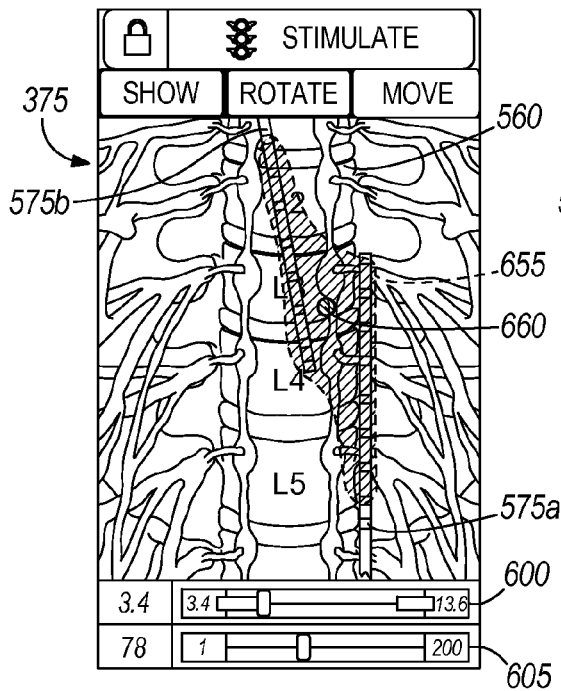
FIGS. 16A-D illustrate a graphical user interface for programming electrical stimulation.
Figure 16B:
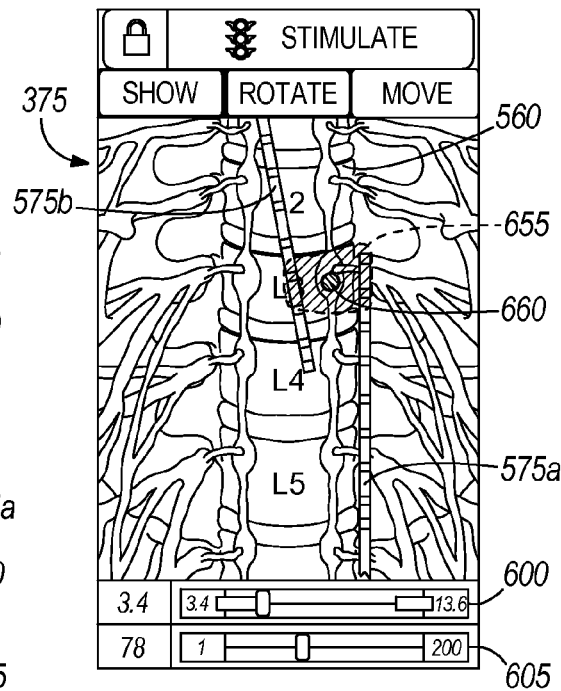
Figure 16C:
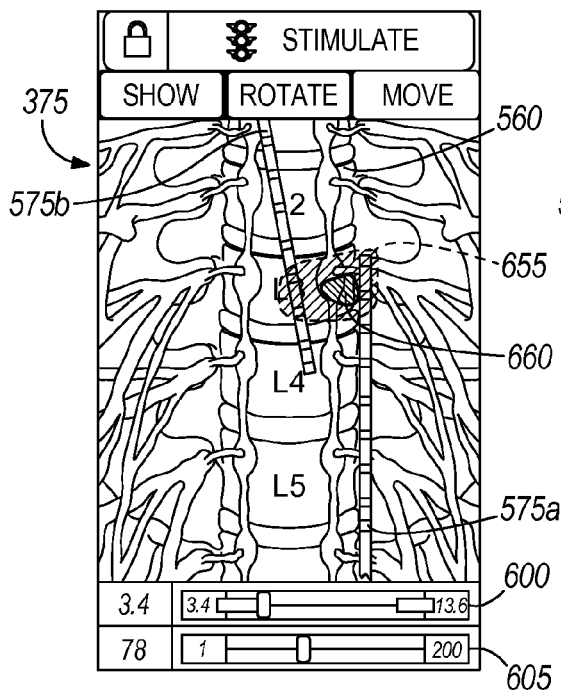

FIGS. 16A and 16B, respectively, show the stimulation field 655 before and after the user modified the shape of the stimulation field 655 to decrease in size. FIGS. 16B and 16C, respectively, show the target 660 before and after the user modified the shape of the target to increase in size. Additionally, FIGS. 16A and 16B, respectively, show the target 660 before and after the user moved the target up and to the right.

Figure 16D:
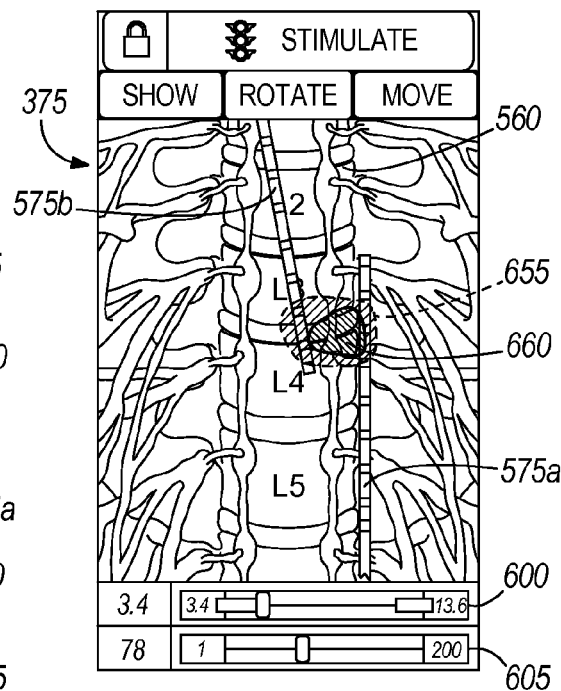

In step 520g, the user is also able to modify the amplitude and pulse width of the stimulation field 655 using the amplitude control 600 and pulse width control 605, as described above with respect to method 510. FIG. 16D depicts an increase in amplitude of the stimulation field 655 and target 660 relative to FIG. 16C caused by a combination of (1) user manipulation of the amplitude control 600 and (2) moving the stimulation field 655 and target 660 downward to an area where the leads 575a and 575b are closer together. In general, the changes in the intensity of the stimulation field 655 and target 660 are illustrated by changing the appearances of each (e.g., by making each more opaque as intensity increases).

Once the user has completed the initial manipulation of the stimulation field 655 and target 660, the user causes generation of an actual stimulation field via the user interface of the CP 130 according to the depicted stimulation field 655 and target 660 as modified by the user in step 520g. To generate the actual stimulation field, stimulation field parameters are determined in step 520h that, if enacted, will cause the depicted stimulation field 655 to be generated. For instance, the CP 130 includes hardware and/or software to determine which electrodes to enable as cathodes, which electrodes to enable as anodes, and the respective electrical signals (e.g., amplitude, pulse width, pulse shape, pulse frequency, and polarity) to send to each to generate the stimulation field 655 and target 660 as depicted after the user's graphical modifications.

In some implementations, the CP 130 assigns a percentage of the total amplitude to each electrode it determines to enable. For instance, lead 575a may have three cathodes assigned with −10%, −80%, and −10%, respectively, while lead 575b has four anodes assigned with 10%, 40%, 40%, and 10%, respectively. Thus, the percentages of the cathodes add up to −100% and the percentages of the anodes add up to 100%, for an overall sum of 0%.

Thereafter, in step 520i, the user causes the IPG 115 to generate stimulation as determined in step 520h. In step 520i, the user unlocks the stimulation lock button 635 and enables the stimulation button 640 as described above. When the stimulate button 640 is enabled, a stop button 645 replaces both the stimulation lock button 635 the stimulate button 640 on the display 375 as shown in FIG. 12H. Additionally, when the stimulate button 640 is enabled, the IPG 115 is instructed to generate stimulation as determined in step 520h.

The user is further able to graphically manipulate the stimulation field 655 and target 660 on-the-fly (i.e., while actual stimulation is on-going). Thus, steps 520g and 520h may be repeated while the IPG 115 is providing stimulation to the patient. Additionally, in some instances, the CP 130 causes generation of a stimulation field (step 520i) before steps 520g and 520h, such that the graphical manipulations occur while the IPG 115 is providing stimulation to the patient.

In some implementations, steps 520g-520i are combined with method 510. That is, in place of steps 520a-520f, method 510 is first used to generate a suggested stimulation field 540 and target 545 as shown in FIG. 15. The suggested stimulation field 540 and target 545 are used in place of the determined and displayed stimulation field 655 and target 660 of step 520f. Thereafter, steps 520g, 520h, and 520i are executed. Thus, the user is able to modify the suggested stimulation field 540 and target 545 in step 520g; the appropriate stimulation parameters are determined to generate the modified (or unmodified) suggested stimulation field 540 and target 545 in step 520h; and the modified (or unmodified) suggested stimulation field and target are generated via the IPG 115 according to the determined stimulation parameters in step 520i.

FIG. 17 depicts a step 525 (also referred to as method 525) for an automated search for an ideal stimulation field based on real-time patient feedback. In step 525a, the patient spinal column 560 is depicted on the display 375 of the CP 130, similar to step 510a and 520a of methods 510 and 520, respectively. In step 525b, positions of medical leads implanted in the patient are determined. For instance, the user of the CP 130 may input the location of the medical leads as described above with respect to steps 510b-510d, and 520b-d in methods 510 and 520, respectively. Additionally, as also described above, the IPG 115 may store the positions of the implanted medical leads. Thus, in step 525b, the IPG 115 may communicate the positions of the implanted medical leads to the CP 130. Images of the leads 575a and 575b are then overlaid on the spinal column 560 according to the medical lead position data obtained from the user, the IPG 115, or another source.

Figure 18A:
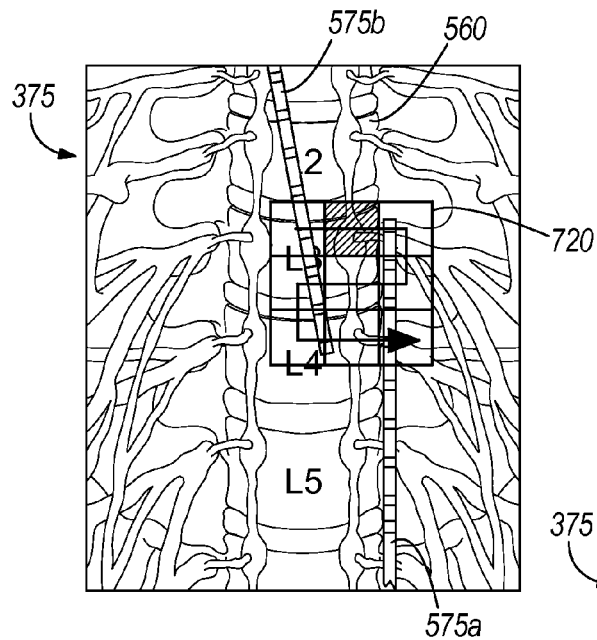
FIGS. 18A-C illustrate a graphical user interface for automated programming.

In step 525c, a set of regions 720 is also overlaid on the spinal column 560 on the display 375. FIG. 18A illustrates the display 375 with the spinal column 560, leads 575a and 575b, and set of regions 720. The set of regions 720 may be positioned over an area where the stimulation is generally expected to help alleviate pain. For instance, based on practitioner experience or the method 505, the CP 130 determines a general area to receive stimulation. Then, the CP 130 overlays the set of regions 720 on the determined general area. The set of regions 720 is depicted in FIG. 18A as a 3×3 grid of squares. However, in some embodiments, the set of regions 720 includes regions of different sizes, shapes (circles, diamonds, rectangles, hexagons, etc.), and/or combinations thereof.

In step 525d, the CP 130 causes the IPG 115 to generate stimulation in each region of the set of regions 720 consecutively. For instance, as shown in FIG. 18A, the CP 130 causes the IPG 115 to generate stimulation in the upper-left region first, and winds down along the path 730 stimulating one square at a time until the last square of the set of regions 720 is stimulated. FIG. 19A illustrates the same path for stimulating each region of the set of regions 720. In FIG. 19A, a stimulation field 735a and target 735b is generated in the top, middle region 740 of the set of regions 720.

As each region of the set of regions 720 is stimulated, the CP 130 receives real-time patient feedback. For instance, the patient 105 indicates via patient feedback device 145 the level of effectiveness of the stimulation of each of the nine regions within the set of regions 720. The IPG 115 and CP 130 may cooperate such that the stimulation field 735a and target 735b are generated for a first region of the set of regions 720, and they remain until the user provides feedback. Once the feedback is received, the CP 130 causes the IPG 115 to generate a stimulation field in the second region. This process continues until each region of the set of regions 720 has been stimulated and each has been associated with user feedback.

Figure 18B:
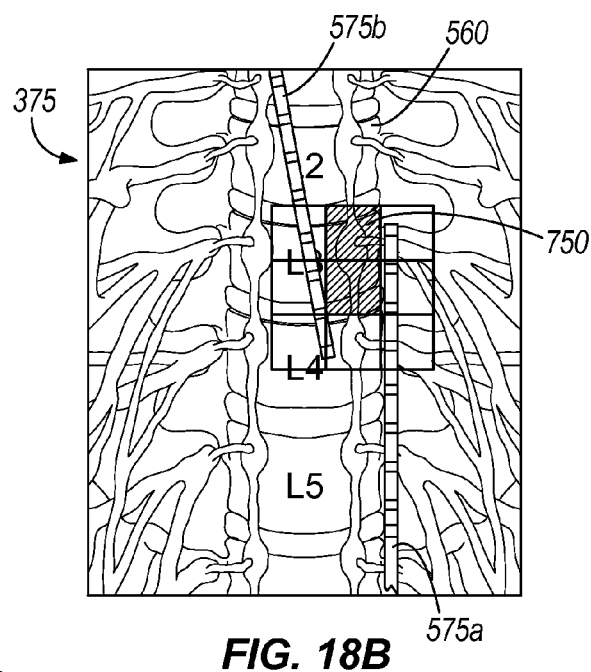

In step 525e, the CP 130 analyzes the patient feedback of step 525d to determine a first subset 750 of the set of regions 720. The first subset 750 includes those regions whose stimulation was most effective in reducing the patient's pain. In FIGS. 18B and 19B, the first subset 750 is highlighted. Determining the first subset 750 may be performed in one or more ways. For instance, the first subset 750 may include the top N regions of the set of regions 720, where N is a number greater than zero and less than the total number of regions within the set of regions 720, or where N is a percentage of the total number of regions within the set of regions 720 (e.g., 25%, which would round to N=2). In some instances, those regions that are below a certain predetermined threshold of effectiveness will not qualify for the first subset 750. Alternatively, any region that is above a predetermined threshold of effectiveness may qualify for the first subset 750.

Figure 18C:
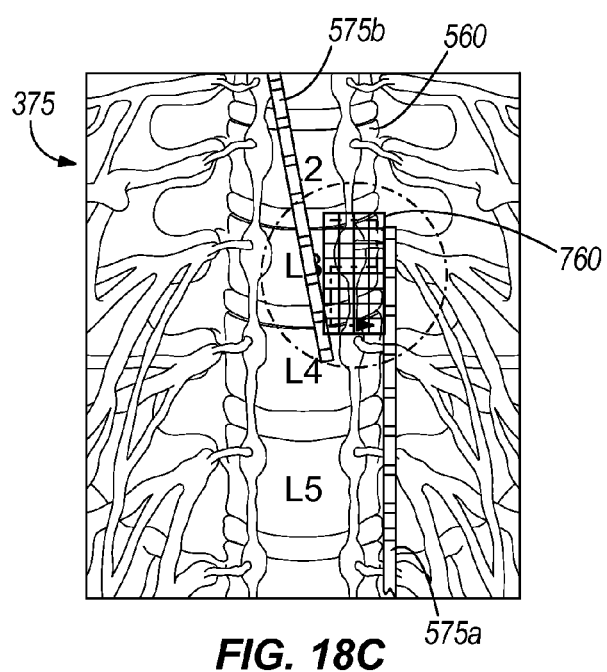
Figure 18D:
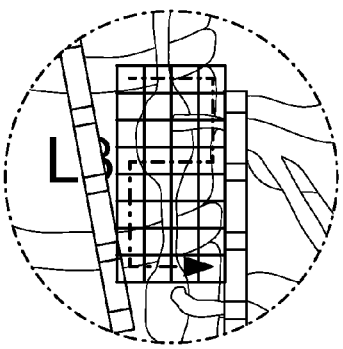
FIG. 18D depicts a close-up view of a portion of the graphical user interface of FIG. 18C.

In step 525f, a set of subregions 760 are displayed within the first subset 750, as illustrated in FIGS. 18C and 19C. FIG. 18D depicts a close-up view of the subregions 760 of FIG. 18C. The set of subregions 760 includes a 2×4 grid of squares that occupy the space of the first subset 750. As with the set of regions 720, the set of subregions 760 can include subregions of different sizes, shapes, and combinations thereof.

In step 525g, the CP 130 causes the IPG 115 to generate stimulation in each subregion of the set of subregions 760 consecutively. For instance, as shown in FIGS. 18C, 18D, and 19C, the CP 130 causes the IPG 115 to generate stimulation in the upper-left subregion first, and then to stimulate one square at a time winding down the path 770 until the last square of the set of subregions 760 is stimulated. In FIG. 19C, a stimulation field 775 (with field 775a and target 775b) is being generated in the top, right subregion 780 of the set of subregions 760.

As each subregion of the set of subregions 760 is stimulated, the CP 130 receives real-time patient feedback similar to the stimulation and feedback described in step 525d for the set of regions 720. For instance, the patient 105 indicates via patient feedback device 145 the level of effectiveness of the stimulation of each of the eight subregions within the set of subregions 760.

In step 525h, the CP 130 analyzes the patient feedback of step 525g to determine a second subset 790 of the set of subregions 760. The second subset 790 includes those subregions whose stimulation was most effective in reducing the patient's pain, similar to the first subset 750. In FIG. 19D, the second subset 790 is highlighted.

In step 525i, the CP 130 determines a stimulation field 800a and target 800b that focuses on the second subset 790. Step 525i is similar to step 520g in that a general graphical outline of a stimulation field is known, and stimulation parameters to cause actual stimulation according to the outline are determined by the CP 130. The CP 130 then provides the stimulation parameters to the IPG 115, which stores them and generates the desired stimulation via the implanted medical leads 110.

The methods 505, 510, 520, and 525 reduce pain in patients through customized stimulation and reduce the time needed for programming of the IPG 115. Additionally, as particular areas are identified to receive targeted stimulation, rather than broad stimulation areas, the stimulation is more efficiently implemented. More efficient stimulation reduces power consumption, which increases the life of batteries within the IPG 115.

Thus, the invention provides, among other things, useful and systems and methods for providing electrical stimulation to a neural tissue of a patient. Various features and advantages of the invention are set forth in the following claims.

What is claimed is:

1. A method of configuring electrical stimulation to treat a patient with a stimulation system, the stimulation system including an electrical stimulation generator, an implanted medical lead implanted in the patient and coupled to the electrical stimulation generator, and a programmer with a display screen, the method comprising:
   receiving a specification of personal anatomical information of the patient, the specification of personal anatomical information comprising at least one of: a height of the patient and a weight of the patient;
   generating an anatomically-correct image of a spinal column of the patient by scaling a standard image of the spinal column based on the received specification of the personal anatomical information of the patient;
   displaying the anatomically-correct image of the spinal column of the patient on the display screen of the programmer;
   determining a position of:
      the implanted medical lead with respect to the anatomically-correct image of the spinal column of the patient,
      an initial stimulation field, and
      an initial target stimulation area within the initial stimulation field;
   displaying the medical lead, the initial stimulation field, and the initial target stimulation area on the anatomically-correct image of the spinal column of the patient, wherein the initial stimulation field has an initial boundary depicted on the display screen and the initial target stimulation area has an initial target boundary depicted on the display screen, wherein the initial target boundary is within the initial boundary;
   receiving, by the programmer, graphical manipulations of the initial boundary and the initial target boundary, wherein the graphical manipulations comprises dragging the initial boundary and the initial target boundary independently on the display screen to define an altered stimulation field and an altered target stimulation area, wherein the initial target boundary remains within the initial boundary and wherein the initial target boundary represents a region of the spinal column of the patient to be stimulated;
   determining stimulation parameters to drive the implanted medical lead to generate the altered stimulation field and the altered target stimulation area; and
   driving, with the electrical stimulation generator, the implanted medical lead according to the determined stimulation parameters.

2. The method of claim 1, further comprising
   receiving, by the programmer, manual adjustments to the stimulation parameters to create modified stimulation parameters; and
   driving, with the electrical stimulation generator, the implanted medical lead according to the modified stimulation parameters.

3. The method of claim 1, further comprising, before receiving the graphical manipulations,
   determining initial stimulation parameters to drive the implanted medical lead to generate the initial stimulation field and the initial target stimulation area; and
   driving, with the electrical stimulation generator, the implanted medical lead according to the initial stimulation parameters.

4. The method of claim 3, wherein the graphical manipulations are received while the electrical stimulation generator is generating electrical stimulation via the implanted medical lead.

5. The method of claim 1, further comprising
   displaying the medical lead, the altered stimulation field, and the altered target stimulation area on the image of the anatomically-correct image of the spinal column of the patient, wherein the altered stimulation field has an altered boundary depicted on the display screen and the altered target stimulation area has an altered target boundary depicted on the display screen;
   receiving, by the programmer, further graphical manipulations of the altered target boundary to define a further altered target stimulation area, wherein the further graphical manipulations at least one of move and alter the shape of the altered target boundary;

determining further stimulation parameters to drive the implanted medical lead to generate the altered stimulation field and the further altered target stimulation area; and driving, with the electrical stimulation generator, the implanted medical lead according to the determined further stimulation parameters.

6. The method of claim 1, further comprising, transmitting, to a memory device implanted in the patient, position data indicating the determined position of the implanted medical lead with respect to the anatomically-correct image of the spinal column of the patient.

7. The method of claim 1, wherein the graphical manipulations of the initial target boundary comprise resizing the initial target boundary.

8. A stimulation system for providing electrical stimulation to treat a patient, the stimulation system comprising:
an electrical stimulation generator;
an implantable medical lead coupled to the electrical stimulation generator; and
a programmer including
a communication unit that communicates with the electrical stimulation generator to program electrical stimulation,
a display screen that displays an anatomically-correct image of a spinal column of the patient and a position of the at least one medical lead relative to the spinal column, and
a user interface,
wherein the programmer:
receives a specification of personal anatomical information of the patient, the specification of personal anatomical information comprising at least one of: a height of the patient and a weight of the patient;
generates the anatomically-correct image of the spinal column of the patient by scaling a standard image of the spinal column based on the received specification of the personal anatomical information of the patient;
determines a position of the implantable medical lead with respect to the spinal column of the patient, an initial stimulation field, and an initial target stimulation area within the initial stimulation field;
displays the medical lead, the initial stimulation field, and the initial target stimulation area on the image of the spinal column of the patient, wherein the initial stimulation field has an initial boundary depicted on the display screen and the initial target stimulation area has an initial target boundary depicted on the display screen, wherein the initial target boundary is within the initial boundary;
receives, by the programmer, graphical manipulations of the initial boundary and the initial target boundary, wherein the graphical manipulations comprises dragging the initial boundary and the initial target boundary independently on the display screen to define an altered stimulation field and an altered target stimulation area, wherein the initial target boundary remains within the initial boundary and wherein the initial target boundary represents a region of the spinal column of the patient to be stimulated;
determines stimulation parameters to drive the implantable medical lead to generate the altered stimulation field and the altered target stimulation area; and
programs the electrical stimulation generator to generate electrical stimulation with the implantable medical lead according to the determined stimulation parameter.

9. The system of claim 8, wherein the programmer further receives manual adjustments to the stimulation parameters to create modified stimulation parameters; and
programs the electrical stimulation generator to generate electrical stimulation with the implantable medical lead according to the modified stimulation parameters.

10. The system of claim 8, wherein the programmer, before receiving the graphical manipulations,
determines initial stimulation parameters to drive the implantable medical lead to generate the initial stimulation field and the initial target stimulation area; and
programs the electrical stimulation generator to generate electrical stimulation with the implantable medical lead according to the initial stimulation parameters.

11. The system of claim 10, wherein the graphical manipulations are received while the electrical stimulation generator is generating electrical stimulation via the implantable medical lead.

12. The system of claim 8, wherein the programmer further displays the medical lead, the altered stimulation field, and the altered target stimulation area on the anatomically-correct image of the spinal column of the patient, wherein the altered stimulation field has an altered boundary depicted on the display screen and the altered target stimulation area has an altered target boundary depicted on the display screen;
receives further graphical manipulations of the altered target boundary to define a further altered target stimulation area, wherein the further graphical manipulations at least one of move and alter the shape of the altered target boundary;
determines further stimulation parameters to drive the implantable medical lead to generate the altered stimulation field and the further altered target stimulation area; and
programs the electrical stimulation generator to generate electrical stimulation with the implantable medical lead according to the determined further stimulation parameters.

13. The system of claim 8, wherein the programmer further transmits, to a memory device implanted in the patient, position data indicating the determined position of the implantable medical lead with respect to the spinal column of the patient.

14. The system of claim 8, wherein the graphical manipulations of the initial target boundary comprise resizing the initial target boundary.

15. A non-transitory computer readable medium including a set of program instructions that, when executed by a processor of a programmer, cause the programmer to:
receive a specification of personal anatomical information of a patient, the specification of personal anatomical information comprising at least one of: a height of the patient and a weight of the patient;
generate an anatomically-correct image of a spinal column of the patient by scaling a standard image of the spinal column based on the received specification of the personal anatomical information of the patient;
display the anatomically-correct image of the spinal column of the patient on a display screen of the programmer;
determine a position of
an implantable medical lead with respect to the spinal column of the patient, an initial stimulation field, and an initial target stimulation area within the initial stimulation field;

display, on the display screen, the medical lead, the initial stimulation field, and the initial target stimulation area on the anatomically-correct image of the spinal column of the patient, wherein the initial stimulation field has an initial boundary depicted on the display screen and the initial target stimulation area has an initial target boundary depicted on the display screen, wherein the initial target boundary is within the initial boundary;

receive, by the programmer, graphical manipulations of the initial boundary and the initial target boundary, wherein the graphical manipulations comprises dragging the initial boundary and the initial target boundary independently on the display screen to define an altered stimulation field and an altered target stimulation area, wherein the initial target boundary remains within the initial boundary and wherein the initial target boundary represents a region of the spinal column of the patient to be stimulated;

determine stimulation parameters to drive the implantable medical lead to generate the altered stimulation field and the altered target stimulation area; and program an electrical stimulation generator to generate electrical stimulation with the implantable medical lead according to the determined stimulation parameters.

16. The non-transitory computer readable medium of claim 15, wherein execution of the instructions by the processor, further cause the programmer to:

receive manual adjustments to the stimulation parameters to create modified stimulation parameters; and program an electrical stimulation generator to generate electrical stimulation with the implantable medical lead according to the modified stimulation parameters.

17. The non-transitory computer readable medium of claim 15, wherein execution of the instructions by the processor, further cause the programmer to, before receiving graphical manipulations, determine initial stimulation parameters to drive the implantable medical lead to generate the initial stimulation field and the initial target stimulation area; and program an electrical stimulation generator to generate electrical stimulation with the implantable medical lead according to the initial stimulation parameters.

18. The non-transitory computer readable medium of claim 17, wherein the graphical manipulations are received while the electrical stimulation generator is generating electrical stimulation via the implantable medical lead.

19. The non-transitory computer readable medium of claim 15, wherein execution of the instructions by the processor, further cause the programmer to transmit, to a memory device implanted in the patient, position data indicating the determined position of the implantable medical lead with respect to the spinal column of the patient.

20. The non-transitory computer readable medium of claim 15, wherein the graphical manipulations of the initial target boundary comprise resizing the initial target boundary.

* * * * *